United States Patent
Odom et al.

(10) Patent No.: US 12,084,421 B2
(45) Date of Patent: Sep. 10, 2024

(54) QUINOLINE-BASED PROTEASOME INHIBITORS AND USES THEREOF

(71) Applicant: Board of Trustees of Michigan State University, East Lansing, MI (US)

(72) Inventors: Aaron Odom, East Lansing, MI (US); Jetze J. Tepe, East Lansing, MI (US); Theresa A. Lansdell, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 717 days.

(21) Appl. No.: 17/167,271

(22) Filed: Feb. 4, 2021

(65) Prior Publication Data
US 2022/0048861 A1 Feb. 17, 2022

Related U.S. Application Data

(63) Continuation of application No. 16/933,898, filed on Jul. 20, 2020, now abandoned, which is a continuation of application No. 15/940,133, filed on Mar. 29, 2018, now Pat. No. 10,752,590.

(60) Provisional application No. 62/479,805, filed on Mar. 31, 2017.

(51) Int. Cl.
| | |
|---|---|
| *C07D 215/06* | (2006.01) |
| *A61K 31/47* | (2006.01) |
| *A61P 35/00* | (2006.01) |

(52) U.S. Cl.
CPC ............ *C07D 215/06* (2013.01); *A61K 31/47* (2013.01); *A61P 35/00* (2018.01)

(58) Field of Classification Search
CPC ........ C07D 215/06; A61K 31/47; A61P 35/00
See application file for complete search history.

(56) References Cited

U.S. PATENT DOCUMENTS

| 5,480,883 A | 1/1996 | Spada et al. |
| 2018/0282280 A1 | 10/2018 | Odom et al. |
| 2020/0347019 A1 | 11/2020 | Odom et al. |

OTHER PUBLICATIONS

Manasanch, E. E.; et al. "Proteasome inhibitors in cancer therapy" 2017, Nat. Rev. Clin. Oncol., vol. 14, pp. 417-433, published online Jan. 24, 2017. (Year: 2017).*
Huang, Z.; et al. "Efficacy of therapy with bortezomib in solid tumors: a review based on 32 clinical trials" 2014, Future Oncology, vol. 10, pp. 1795-1807. (Year: 2014).*
Tabas, I.; Glass, C. K. "Anti-Inflammatory Therapy in Chronic Disease: Challenges and Opportunities" 2013, Science, vol. 339, pp. 166-172. (Year: 2013).*
Zhu, Y.; et al. "Synthesis, in Vitro and in Vivo Biological Evaluation, Docking Studies, and Structure-Activity Relationship (SAR) Discussion of Dipeptidyl Boronic Acid Proteasome Inhibitors Composed of β-Amino Acids" 2010, J. Med. Chem., vol. 53, pp. 1990-1999. (Year: 2010).*
Pubchem CID 105484078 (3-cyclohexyl-6-quinolinamine ), Available in PubChem database Jan. 13, 2016. (Accessed Jan. 9, 2024). (Year: 2016).*
"U.S. Appl. No. 15/940,133, Final Office Action mailed Aug. 19, 2019", 21 pgs.
"U.S. Appl. No. 15/940,133, Non Final Office Action mailed Jan. 9, 2020", 8 pgs.
"U.S. Appl. No. 15/940,133, Non Final Office Action mailed Feb. 27, 2019", 36 pgs.
"U.S. Appl. No. 15/940,133, Notice of Allowance mailed Apr. 16, 2020", 6 pgs.
"U.S. Appl. No. 15/940,133, Response filed Apr. 9, 2020 to Non Final Office Action mailed Jan. 9, 2020", 6 pgs.
"U.S. Appl. No. 15/940,133, Response Filed May 24, 2019 to Non-Final Office Action Mailed Feb. 27, 2019", 12 pgs.
"U.S. Appl. No. 15/940,133, Response filed Nov. 20, 2018 to Restriction Requirement mailed Sep. 20, 2018", 10 pgs.
"U.S. Appl. No. 15/940,133, Response filed Nov. 26, 2019 to Final Office Action mailed Aug. 19, 2019", 10 pgs.
"U.S. Appl. No. 15/940,133, Restriction Requirement mailed Sep. 20, 2018", 7 pgs.
"U.S. Appl. No. 16/933,898, Non Final Office Action mailed Aug. 6, 2020", 16 pgs.
Brayer, et al., "The Potential of Ixazomib, a Second-Generation Proteasome Inhibitor, in the Treatment of Multiple Myeloma", Ther Adv Hematol , vol. 8(7), (2017), 209-220 pgs.
Cromm, et al., "The Proteasome in Modern Drug Discovery: Second Life of a Highly Valuable Drug Target", ACS Cent. Sci. 3, (2017), 830-838 pgs.
Dermer, et al., "Another Anniversary for the War on Cancer", Bio/Technology, 12, (1994), 8 pgs.
Freshney, R. I, "Culture of Animal Cells, A Manual of Basic Technique", Alan R. Liss, Inc, Newyork, (1983), 7 pgs.
Golub, T. R., et al., "Molecular Classification of Cancer: Class Discovery and Class Prediction by Gene Expression Monitoring", Science, vol. 286, (Oct. 15, 1999), 531-537.
Majumder, Supriyo, et al., "A Multicomponent Coupling Sequence for Direct Access to Substituted Quinolines", Organic Letters vol. 11, No. 20, (Aug. 10, 2009), 4720-4723.
McDaniel, Tanner J, et al., "Substituted quinolines as noncovalent proteasome inhibitors", Bioorganic & Medicinal Chemistry 24, (2016), 2441-2450.

(Continued)

*Primary Examiner* — Eric Olson
*Assistant Examiner* — Benjamin M Brandsen
(74) *Attorney, Agent, or Firm* — Schwegman Lundberg & Woessner, P.A.

(57) ABSTRACT

Described herein are quinoline compounds useful for, among other things, inhibition of the proteasome and for treatment of cancer and inflammation.

19 Claims, No Drawings

(56) References Cited

OTHER PUBLICATIONS

"3-[(1E)-cycloocten-1-yl]quinoline", PubChem_Compound-Compound-CID 101228022, (Dec. 18, 2015).
"3-cycloheptylquinoline", PubChem_Compound-Compound_CID 66524652, (Oct. 20, 2012).
"3-quinolin-3-ylcyclohept-2-en-1-amine", PubChem_Compound-Compund_CID 107383271, (Jan. 15, 2016).
"3-(cyclohexen-1-yl)quinoline", PubChem_Compound-Compound_CID 21822133, (Dec. 5, 2007).
"3-cyclohexylquinoline", PubChem_Compound-Compound_CID 23056528, (Dec. 5, 2007).
"3-phenylquinoline", PubChem_Compound-Compound_CID 282849, (Mar. 26, 2005).
"3-quinolin-3-ylcyclohept-2-en-1-ol", PubChem_Compound-Compound_CID 107383467, (Jan. 15, 2016).
"3-(3-chlorocyclohepten-1-yl)quinoline", PubChem_Compound-Compound_CID 107384072, (Jan. 15, 2016).
Simone, J.V. "Cecil Textbook of Medicine", 20th edition, vol. 1, (1996), 1004-1010 pgs.

\* cited by examiner

QUINOLINE-BASED PROTEASOME INHIBITORS AND USES THEREOF

CROSS-REFERENCE TO RELATED APPLICATIONS

This application continuation of U.S. patent application Ser. No. 16/933,898, filed Jul. 20, 2020, which is a continuation of U.S. patent application Ser. No. 15/940,133, filed Mar. 29, 2018, which application claims the benefit of priority of U.S. Provisional Appl. Ser. No. 62/479,805, filed Mar. 31, 2017, which is incorporated by reference as if fully set forth herein.

STATEMENT OF GOVERNMENT SUPPORT

This invention was made with government support under CHE1265738 awarded by the National Science Foundation. The government has certain rights in the invention.

BACKGROUND

The human proteasome may be a target for the treatment of cancers such as multiple myeloma (MM) and relapsed/refractory mantle cell lymphoma (MCL). Current therapeutics for these diseases include compounds that target the proteasomes in the cancerous cells. However, the available therapeutic compounds are competitive inhibitors that bind through a covalent and irreversible (or slowly reversible) bond to the N-terminal threonine of the enzyme's catalytic sites. And unfortunately, more than 97% of multiple myeloma patients develop resistance or become intolerant to the currently available competitive inhibitors within a few years, after which survival is often less than one year. Further, examples of small molecules that act as non-competitive proteasome inhibitors are very scarce and exhibit activity only at high micromolar concentrations or non-physiologically relevant concentrations.

SUMMARY

Described herein are compounds that can be useful for overcoming the types of acquired resistance often exhibited by cancerous cells. Moreover, the compounds described herein can be active at low micromolar or nanomolar concentrations. Therefore, as provided herein, non-competitive proteasome inhibitors are now available at useful dosages for treatment of cancer and inflammatory disease that avoid the problems of cellular drug resistance and minimize side effects.

The disclosure relates to a compound of formula I:

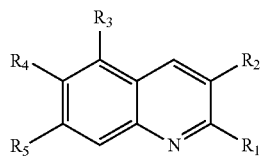

wherein:
$R_1$ is hydrogen or lower alkyl;
$R_2$ is hydrogen, halogen (e.g., Cl, Br, or I), alkyl, alkoxy, cycloheteroalky or 4-8 carbon cycloalkyl with 0-2 unsaturated bonds;
$R_3$ is hydrogen, halogen (e.g., Cl, Br, F, or I), or lower alkyl;
$R_4$ is hydrogen, halogen (e.g., Cl, Br, F, or I), hydroxy, lower alkyl, alkoxy, aminoalkyl, 4-8 carbon cycloheteroalkyl; and
$R_5$ is hydrogen, halogen (e.g., Cl, Br, or I), lower alkyl, or lower alkoxy.

In some cases, the cycloalkyl or cycloheteroalkyl, groups can be substituted, for example, with one to three hydroxy, halogen, lower alkyl, amino, or amino alkyl groups.

DESCRIPTION

The disclosure relates to improved quinoline compounds that are biologically active inhibitors of mammalian proteasomes. The quinoline compounds described herein are useful for treatment of a variety of diseases and conditions, including cancer and inflammatory conditions. The compounds can have the formula I:

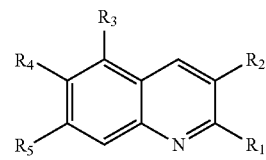

wherein:
$R_1$ is hydrogen or lower alkyl;
$R_2$ is hydrogen, halogen (e.g., Cl, Br, or I), alkyl, alkoxy, cycloheteroalky or 4-8 carbon cycloalkyl with 0-2 unsaturated bonds;
$R_3$ is hydrogen, halogen (e.g., Cl, Br, F, or I), or lower alkyl;
$R_4$ is hydrogen, halogen (e.g., Cl, Br, F, or I), hydroxy, lower alkyl, alkoxy, aminoalkyl, 4-8 carbon cycloheteroalkyl; and
$R_5$ is hydrogen, halogen (e.g., Cl, Br, or I), lower alkyl, or lower alkoxy.

The cycloalkyl or cycloheteroalkyl, groups can be substituted, for example, with one to three hydroxy, halogen, lower alkyl, amino, or amino alkyl groups.

The compounds can also be compounds of the formula II:

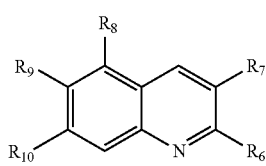

wherein:
$R_6$ is hydrogen, alkyl or aryl;
$R_7$ is hydrogen, alkyl, alkenyl, cycloalkyl, aryl, cycloheteroalkyl or alkoxy;
$R_8$ is hydrogen, halogen (e.g., Cl, Br, F, or I), or alkyl;
$R_9$ is hydrogen, halogen (e.g., Cl, Br, F, or I), hydroxy, alkyl, alkoxy, aminoalkyl or heterocyclyl; and
$R_{10}$ is hydrogen, halogen (e.g., Cl, Br, F, or I), alkyl, or alkoxy.

The compounds can also be compounds of the formula III:

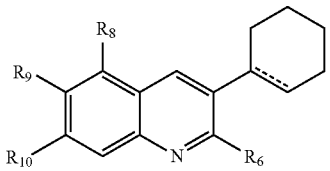

wherein:
the dashed line can be absent or represents a double bond;
$R_6$ is hydrogen, alkyl or aryl;
$R_8$ is hydrogen, halogen (e.g., Cl, Br, F, or I), or alkyl;
$R_9$ is hydrogen, halogen (e.g., Cl, Br, F, or I), hydroxy, alkyl, alkoxy, aminoalkyl or heterocyclyl; and
$R_{10}$ is hydrogen, halogen (e.g., Cl, Br, F, or I), alkyl, or alkoxy.

The compounds can also be compounds of the formula IV:

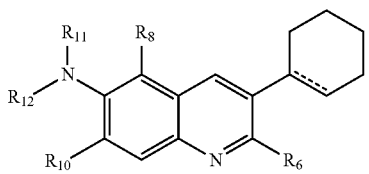

wherein:
the dashed line can be absent or represents a double bond;
$R_6$ is hydrogen, alkyl or aryl;
$R_8$ is hydrogen, halogen (e.g., Cl, Br, F, or I), or alkyl;
$R_{10}$ is hydrogen, halogen (e.g., Cl, Br, F, or I), alkyl, or alkoxy; and
$R_{11}$ and $R_{12}$ are each, independently, hydrogen or alkyl or, $R_{11}$ and $R_{12}$, together with the nitrogen atom to which they are attached, form a heterocyclyl group optionally containing one additional heteroatom (e.g., S, O or N).

The compounds can also be compounds of the formula V:

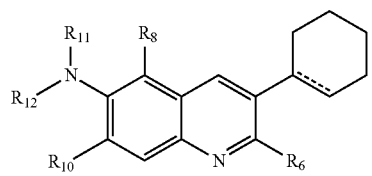

wherein:
the dashed line can be absent or represents a double bond;
$R_6$ is hydrogen or alkyl;
$R_8$ is hydrogen, halogen (e.g., Cl, Br, F, or I), or alkyl;
$R_{10}$ is hydrogen, halogen (e.g., Cl, Br, F, or I), alkyl, or alkoxy; and
$R_{11}$ and $R_{12}$ are each, independently, hydrogen or alkyl or, $R_{11}$ and $R_{12}$, together with the nitrogen atom to which they are attached, form a heterocyclyl group optionally containing one additional heteroatom (e.g., S, O or N).

In the compounds of the formula I, $R_1$ can be hydrogen or alkyl, such as methyl or ethyl or, in the compounds of the formula II-V, $R_6$ can be hydrogen or alkyl, such as methyl or ethyl. At the same time, or alternatively, in the compounds of the formula I, $R_2$ can be cycloxexyl or cyclohexenyl, such as the group:

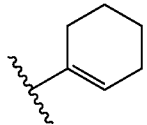 [SMILES: *C1=CCCCC1]

or, in the compounds of the formula II-V, $R_7$ can be cycloxexyl or cyclohexenyl, such as the group:

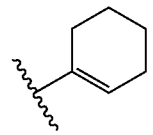

At the same time, or alternatively, in the compounds of the formula I, $R_3$ can be hydrogen, alkyl, such as methyl, or alkoxy, such as methoxy or, in the compounds of the formula II-V, $R_8$ can be hydrogen, alkyl, such as methyl, or alkoxy, such as methoxy. At the same time, or alternatively, in the compounds of the formula I, $R_4$ can be hydrogen, alkyl, such as methyl, isopropyl or butyl, alkoxy, such as methoxy, aminoalkyl, such as N,N-dimethylamino or a heterocyclo group optionally containing one additional heteroatom (e.g., piperidinyl or morpholinyl) or, in the compounds of the formula II-V, $R_9$ can be can be hydrogen, alkyl, such as methyl, isopropyl or butyl, alkoxy, such as methoxy, aminoalkyl, such as N,N-dimethylamino or a heterocyclo group optionally containing one additional heteroatom (e.g., piperidinyl or morpholinyl). At the same time, or alternatively, in the compounds of the formula I, $R_5$ can be hydrogen, alkyl, such as methyl or alkoxy, such as methoxy or, in the compounds of the formula II-V, $R_{10}$ can be hydrogen, alkyl, such as methyl or alkoxy, such as methoxy. In short, it is clear that each embodiment described herein is envisaged to be applicable in each combination with other embodiments described herein. For example, embodiments corresponding to formula I are equally envisaged as being applicable to formulae II-V.

This disclosure contemplates compounds of the formulae I-V having an $IC_{50}$ of less than 100 µM, less than 50 µM, less than 25 µM, less than 10 µM, less than 5 µM, less than 1 µM, less than 500 nM, less than 250 nM, less than 100 nM or less than 10 nM; for example compounds having an $IC_{50}$ of from about 10 nM to about 10 µM, about 100 nM to about 1 µM, about 500 nM to about 10 µM, about 1 µM to about 20 µM or about 1 µM to about 10 µM.

An alkyl includes straight chain and branched, substituted or unsubstituted alkyl groups having from 1 to about 20 carbon atoms, 1 to 12 carbons, from 1 to 8 carbon atoms or from 1 to about 6 carbon atoms (also referred to herein as "lower alkyl" in reference to alkyl and alkoxy groups). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Lower alkyl groups include straight chain and branched alkyl groups having from 1 to about 6 carbon atoms. Representative substituted alkyl groups can be substituted one or more times with, for example, cycloalkyl, heterocyclyl, aryl, amino, haloalkyl, hydroxy, cyano, carboxy, nitro, thio, alkoxy, and halogen groups. As further example, representative substituted alkyl groups can be substituted one or more fluoro, chloro, bromo, iodo, amino, amido, alkyl, alkoxy, alkenyl, alkynyl, alkoxycarbonyl, aryloxy, carboxy, haloalkyl, hydroxy, cyano, nitro, trifluoromethyl or trifluoromethoxy.

The term "alkenyl" as used herein refers to substituted or unsubstituted straight chain or branched groups having at least one carbon-carbon double bond and from 2 to 20 carbon atoms, 10 to 20 carbon atoms, 12 to 18 carbon atoms, 6 to about 10 carbon atoms, 2 to 10 carbons atoms, 2 to 8 carbon atoms, 3 to 8 carbon atoms, 4 to 8 carbon atoms, 5 to 8 carbon atoms, 2 to 6 carbon atoms, 3 to 6 carbon atoms, 4 to 6 carbon atoms, 2 to 4 carbon atoms, or 2 to 3 carbon atoms. The double bonds can be be trans or cis orientation. The double bonds can be terminal or internal. The alkenyl group can be attached via the portion of the alkenyl group containing the double bond, e.g., vinyl, propen-1-yl and buten-1-yl, or the alkenyl group can be attached via a portion of the alkenyl group that does not contain the double bond, e.g., penten-4-yl. Examples of $(C_2-C_{20})$-alkenyl groups include those with from 1 to 8 carbon atoms such as vinyl, propenyl, propen-1-yl, propen-2-yl, butenyl, buten-1-yl, buten-2-yl, sec-buten-1-yl, sec-buten-3-yl, pentenyl, hexenyl, heptenyl and octenyl groups. Examples of branched $(C_2-C_{20})$-alkenyl groups include isopropenyl, iso-butenyl, sec-butenyl, t-butenyl, neopentenyl, and isopentenyl. It is envisaged that alkenyl can also include "masked" alkenyl groups, precursors of alkenyl groups or other related groups. As such, compounds are also envisaged where a carbon-carbon double bond of an alkenyl is replaced by an epoxide or aziridine ring. Substituted alkenyl groups can be substituted one or more times with cycloalkyl, heterocyclyl, aryl, amino, haloalkyl, hydroxy, cyano, carboxy, nitro, thio, alkoxy, and halogen groups. As further example, representative substituted alkyl groups can be substituted one or more fluoro, chloro, bromo, iodo, amino, amido, alkyl, alkoxy, alkenyl, alkynyl, alkoxycarbonyl, aryloxy, carboxy, haloalkyl, hydroxy, cyano, nitro, trifluoromethyl or trifluoromethoxy.

The term "aryl" as used herein refers to substituted or unsubstituted univalent groups that are derived by removing a hydrogen atom from an arene, which is a cyclic aromatic hydrocarbon, having from 6 to 20 carbon atoms, 10 to 20 carbon atoms, 12 to 20 carbon atoms, 6 to about 10 carbon atoms or 6 to 8 carbon atoms. Examples of $(C_6-C_{20})$aryl groups include phenyl, napthalenyl, azulenyl, biphenylyl, indacenyl, fluorenyl, phenanthrenyl, triphenylenyl, pyrenyl, naphthacenyl, chrysenyl, anthracenyl groups. Examples include substituted phenyl, substituted napthalenyl, substituted azulenyl, substituted biphenylyl, substituted indacenyl, substituted fluorenyl, substituted phenanthrenyl, substituted triphenylenyl, substituted pyrenyl, substituted naphthacenyl, substituted chrysenyl, and substituted anthracenyl groups. Examples also include unsubstituted phenyl, unsubstituted napthalenyl, unsubstituted azulenyl, unsubstituted biphenylyl, unsubstituted indacenyl, unsubstituted fluorenyl, unsubstituted phenanthrenyl, unsubstituted triphenylenyl, unsubstituted pyrenyl, unsubstituted naphthacenyl, unsubstituted chrysenyl, and unsubstituted anthracenyl groups. Aryl includes phenyl groups and also non-phenyl aryl groups. From these examples, it is clear that the term $(C_6-C_{20})$aryl encompasses mono- and polycyclic $(C_6-C_{20})$aryl groups, including fused and non-fused polycyclic $(C_6-C_{20})$aryl groups. Substituted aryl groups can be substituted one or more times with cycloalkyl, heterocyclyl, aryl, amino, haloalkyl, hydroxy, cyano, carboxy, nitro, thio, alkoxy, and halogen groups. As further example, representative substituted alkyl groups can be substituted one or more fluoro, chloro, bromo, iodo, amino, amido, alkyl, alkoxy, alkenyl, alkynyl, alkoxycarbonyl, aryloxy, carboxy, haloalkyl, hydroxy, cyano, nitro, trifluoromethyl or trifluoromethoxy.

The term "heterocyclyl" and "cycloheteroalkyl" are used interchangeably herein and refer to substituted non-aromatic and unsubstituted non-aromatic rings containing 3 or more atoms in the ring, of which, one or more is a heteroatom such as, but not limited to, N, O, and S. In some examples, heterocyclyl groups include heterocyclyl groups that include 3 to 8 carbon atoms $(C_3-C_8)$, 3 to 6 carbon atoms $(C_3-C_6)$ or 6 to 8 carbon atoms $(C_6-C_8)$. A heterocyclyl group designated as a $C_2$-heterocyclyl can be a 5-membered ring with two carbon atoms and three heteroatoms, a 6-membered ring with two carbon atoms and four heteroatoms and so forth. Likewise a $C_4$-heterocyclyl can be a 5-membered ring with one heteroatom, a 6-membered ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused non-aromatic groups. Representative heterocyclyl groups include, but are not limited to piperidynyl, piperazinyl, morpholinyl, furanyl, and pyrrolidinyl. For example, heterocyclyl groups include, without limitation:

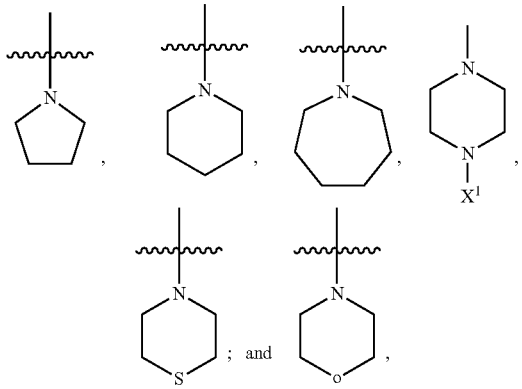

wherein $X^1$ represents H, $(C_1-C_{20})$alkyl, $(C_6-C_{20})$aryl or an amine protecting group (e.g., a t-butyloxycarbonyl group) and wherein the heterocyclyl group can be substituted or unsubstituted. A nitrogen-containing heterocyclyl group is a heterocyclyl group containing a nitrogen atom as an atom in the ring.

A cycloalkyl is an alkyl in cyclic, or ring form. Such a cycloalkyl can have 3-10 carbon atoms or 3-6 carbon atoms. Representative saturated cyclic alkyls (i.e., cycloalkyls) include cyclopropyl, cyclobutyl, cyclopentyl, cyclohexyl, and the like; while unsaturated cyclic alkyls include cyclopentenyl and cyclohexenyl, and the like. Cyclic alkyls can also be referred to as "cycloalkyls" or "homocycles" or "homocyclic rings."

"Heterocycloalkyl" means an cycloalkyl having at least one alkyl carbon atom replaced with a heterocycle, such as —$CH_2$— replaced by an oxygen, a nitrogen (e.g., NH), and the like.

The term "alkoxy" refers to an oxygen atom connected to an alkyl group, as is defined herein. Examples of alkoxy groups include but are not limited to methoxy, ethoxy, propoxy, butoxy, pentyloxy, hexyloxy, and the like. Examples of branched alkoxy groups include but are not limited to isopropoxy, sec-butoxy, tert-butoxy, isopentyloxy, isohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein.

"Halogen" as the term is used herein includes fluoro, chloro, bromo, and iodo.

The term "amino" as used herein refers to a substituent of the form $-NH_2$, $-NHR$, $-NR_2$, $-NR_3^+$, wherein each R is independently selected, and protonated forms of each, except for $-NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The term "carboxy" as used herein refers to a group containing a carbonyl moiety wherein the group is bonded via the carbonyl carbon atom. The carbonyl carbon atom is also bonded to a hydroxy group or oxygen anion so as to result in a carboxylic acid or carboxylate. Carboxy also includes both the protonated form of the carboxylic acid and the salt form. For example, carboxy can be understood as COOH or $CO_2H$.

In some instances, the compounds described herein can contain chiral centers. All diastereomers of the compounds described herein are contemplated herein, as well as racemates. In addition, the compounds described herein can be salts, solvates or prodrugs.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric (or larger) amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

This disclosure also contemplates pharmaceutical compositions comprising one or more compounds and one or more pharmaceutically acceptable excipients. A "pharmaceutical composition" refers to a chemical or biological composition suitable for administration to a subject (e.g., mammal). Such compositions can be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" is a carrier, sometimes a liquid, in which an active therapeutic agent is formulated. The excipient generally does not provide any pharmacological activity to the formulation, though it can provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes, but is not limited to, any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions can be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions of the present invention can be orally administered as a capsule (hard or soft), tablet (film coated, enteric coated or uncoated), powder or granules (coated or uncoated) or liquid (solution or suspension). The formulations can be conveniently prepared by any of the methods well-known in the art. The pharmaceutical compositions of the present invention can include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various embodiments of the present invention can vary according to factors such as the disease state, age, gender, weight, patient history, risk factors, predisposition to disease, administration route, pre-existing treatment regime (e.g., possible interactions with other medications), and weight of the subject. Dosage regimens can be adjusted to provide the optimum therapeutic response. For example, a single bolus can be administered, several divided doses can be administered over time, or the dose can be proportionally reduced or increased as indicated by the exigencies of therapeutic situation.

A "dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in subjects. In therapeutic use for treatment of conditions in mammals (e.g., humans) for which the compounds of the present invention or an appropriate pharmaceutical composition thereof are effective, the compounds of the present invention can be administered in an effective amount. The dosages as suitable for this invention can be a composition, a pharmaceutical composition or any other compositions described herein.

For each of the recited embodiments, the dosage is typically administered once, twice, or thrice a day, although more frequent dosing intervals are possible. The dosage can be administered every day, every 2 days, every 3 days, every 4 days, every 5 days, every 6 days, and/or every 7 days (once a week). In one embodiment, the dosage can be administered daily for up to and including 30 days, preferably between 7-10 days. In another embodiment, the dosage can be administered twice a day for 10 days. If the patient requires treatment for a chronic disease or condition, the dosage can be administered for as long as signs and/or symptoms persist. The patient can require "maintenance treatment" where the patient is receiving dosages every day for months, years, or the remainder of their lives. In addition, the composition of this invention can be to effect prophylaxis of recurring symptoms. For example, the dosage can be administered once or twice a day to prevent the onset of symptoms in patients at risk, especially for asymptomatic patients.

The absolute weight of a given compound included in a unit dose for administration to a subject can vary widely. For example, about 0.0001 to about 1 g, or about 0.001 to about 0.5 g, of at least one compound of this disclosure, or a plurality of compounds can be administered. Alternatively, the unit dosage can vary from about 0.001 g to about 2 g, from about 0.005 g to about 0.5 g, from about 0.01 g to about 0.25 g, from about 0.02 g to about 0.2 g, from about 0.03 g to about 0.15 g, from about 0.04 g to about 0.12 g, or from about 0.05 g to about 0.1 g.

Daily doses of the compounds can vary as well. Such daily doses can range, for example, from about 0.01 g/day to about 10 g/day, from about 0.02 g/day to about 5 g/day, from about 0.03 g/day to about 4 g/day, from about 0.04 g/day to about 3 g/day, from about 0.05 g/day to about 2 g/day, and from about 0.05 g/day to about 1 g/day.

It will be appreciated that the amount of compound(s) for use in treatment will vary not only with the particular carrier selected but also with the route of administration, the nature of the condition being treated, and the age and condition of the patient. Ultimately the attendant health care provider may determine proper dosage.

The compositions described herein can be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to, for example, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

The compositions can include the compounds described herein in a "therapeutically effective amount." Such a therapeutically effective amount is an amount sufficient to obtain the desired physiological effect, such as a reduction of at least one symptom of cancer or an inflammatory disease or condition.

The compositions can contain other proteasome inhibitors such as Bortezomib™ and Carfilzomib™ as well as other therapeutic agents. For example, the compositions can contain other ingredients such as chemotherapeutic agents, anti-inflammatory agents, anti-viral agents, antibacterial agents, antimicrobial agents, immunomodulatory drugs, such as lenalidomide, pomalidomide or thalidomide, histone deacetylase inhibitors, such as panobinostat, preservatives or combinations thereof.

Examples of additional therapeutic agents that may be used include, but are not limited to: other proteasome inhibitors, alkylating agents, such as nitrogen mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as paclitaxel (Taxol®), docetaxel (Taxotere®), and epothilones A-F or their analogs or derivatives; plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators, and monoclonal antibodies.

Examples of chemotherapeutic agents that may be co-administered with the compounds described include compounds that induce apoptosis, compounds that reduce the lifespan of cancer cells, compounds that render cells sensitive to stress, as well as any available anti-cancer agents. Examples of agents that can be included in the compositions described herein, or that can be co-administered with the compounds described herein include: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

The compounds can also be used in conjunction with radiation therapy.

The compounds described herein can be co-administrated with other proteasome inhibitors such as Bortezomib™ and Carfilzomib™ as well as other therapeutic agents.

This disclosure also includes methods for treating cancer, including the symptoms of cancer, comprising administering a therapeutically effective amount of at least one of the compounds described herein (e.g., compounds of the formulae I-V) to a subject in need thereof. This disclosure also includes methods for treating an inflammatory disease, including the symptoms of an inflammatory disease, comprising administering a therapeutically effective amount of at least one of the compounds described herein (e.g., compounds of the formulae I-V) to a subject in need thereof. This disclosure also includes methods for treating graft-versus-host disease, including the symptoms of graft-versus-host disease, comprising administering a therapeutically effective amount of at least one of the compounds described herein (e.g., compounds of the formulae I-V) to a subject in need thereof.

"Subject" means any animal, for example, a human patient, livestock, zoo animal, or domestic pet.

As used herein, the terms "treat" and "treating" are not limited to the case where the subject (e.g. patient) is cured and the disease is eradicated. Rather, treatment that merely reduces symptoms, and/or delays disease progression is also contemplated.

"Cancer" means any of various cellular diseases with malignant neoplasms characterized by the proliferation of anaplastic cells. It is not intended that the diseased cells must actually invade surrounding tissue and metastasize to new body sites. Cancer can involve any tissue of the body and have many different forms in each body area. Many cancers are named for the type of cell or organ in which they start. As used herein, the term "cancer" also encompasses blood related cancers, such as multiple myeloma and leukemia.

Whether "cancer is reduced" can be identified by a variety of diagnostic manners known to one skill in the art including, but not limited to, observation the reduction in tumor size, or number of cancer cells, or number of tumor masses, or an increase of apoptosis of cancer cells. Cancer can be reduced (or apoptosis increased) by more than a 5%, or more than 10%, or more than 20%, or more than 25%, or more than 50%. Such a reduction in cancer or increase in apoptosis of cancer cells can be observed after administration or exposure to selected compound (e.g., an quinoline compound described herein) compared to a control subject or sample not administered or contacted without the compound. Reduction in cancer or increase in apoptosis of cancer cells can also be identified by a change in relevant biomarker or gene expression profile, such as PSA for prostate cancer, her2 for breast cancer, or others.

For example, reduction of cancer may be identified in vitro using the following conditions for evaluation of apoptosis: i) Jurkat human T-cell leukemia cells are passed into flasks (250 mL, 75 cm$^2$) with 20 mL of supporting media; ii) after incubation at 37° C. with 5% $CO_2$, sample compound (or for a control, no compound) is added to a flask at a selected concentration (e.g., 1 nanomolar to 1 millimolar), and cells are incubated for another day; iii) cells are treated with 10 µM camptothecin and incubated with SYTOX Green reagent and annexin V allophycocyanin (APC) conjugate (Invitrogen) and iv) Flow cytometry at 488 nm and 633 nm excitation. In cells undergoing apoptosis, phosphatidylserine (PS) is transferred from the cytoplasmic surface of the cell membrane to the outer leaflet. Annexin V has a high affinity for phosphatidylserine and dye conjugates provide an indication of apoptosis by phosphatidylserine exposure and membrane integrity.

Symptoms of cancer include fatigue, increased risk of infection, renal failure, anemia, confusion, headaches, lymph node swelling or lumps, loss of appetite, vomiting, diarrhea, and combinations thereof. Symptoms of an inflammatory disease or condition can include joint pain, swollen joints, muscle stiffness, headaches, fever, chills, loss of appetite, systemic pain or aches.

Examples of cancers that can be treated by administration of the compounds described herein include cancers of the blood, bone, bone marrow, brain, breast, cervix, intestine, kidney, liver, lung, nervous system, ovaries, pancreas, prostate, skin, testis and combinations thereof. The cancer can be benign or malignant. The cancer can be a hormone-dependent cancer such as a breast, prostate, testicular, or ovarian cancer. The cancer can be a lymphoma, myeloma, or leukemia. In some instances, the cancer is multiple myeloma or relapsed/refractory mantle cell lymphoma The cancer treated by the compounds and methods described herein can be a hematological cancer, lymphatic cancer, breast cancer, cervical cancer, ovarian cancer, prostate cancer, testicular cancer, pancreatic cancer, gastrointestinal cancer, neurological cancer, skin cancer, bone cancer, or a combination thereof.

Cancers can be treated by administering one or more of the compounds described herein systemically or locally. For example, the compounds can be administered orally, into the blood stream, into a tumor, into a cancerous site, or into the bone marrow. Benign cell growth can also be treated, e.g., warts, by systemic or local administration. In another embodiment, cells can be obtained from a subject, treated ex vivo with the compounds described herein, optionally in combination with other agents or cytotoxins, to remove certain undesirable cells, e.g., cancer cells, and administered back to the same or a different subject.

Inflammatory diseases that can be treated by the compounds and methods described herein include, but are not limited to, autoimmune disease, chronic obstructive pulmonary disease (COPD); osteoarthritis (OA); rheumatoid arthritis (RA); inflammatory bowel disease (IBD); inflammatory bone destruction, psoriasis; and atherosclerosis.

Chronic obstructive pulmonary disease (COPD) is a group of progressive lung diseases characterized by airflow obstruction or limitation that is not fully reversible. The restricted airflow is generally progressive and associated with abnormal inflammatory response of the lungs to irritants. The family of COPD diseases includes chronic bronchitis, emphysema and bronchiectasis.

Osteoarthritis (OA) is characterized by mild to debilitating pain, which can involve almost any joint but, in particular, weight bearing joints such as the hip, knee, spine and feet. Osteoarthritis refers to a degeneration of the articular cartilage that makes up the joint surface. This breakdown removes the soft buffer between the bones and can, when severe, result in bone against bone friction, which can cause severe pain and loss of movement. Symptoms include joint pain or aching—at the time of exercise but also when resting if the osteoarthritis is severe, and reduced movement and progressive stiffness of the joint.

Rheumatoid arthritis (RA) is a chronic systemic inflammatory disease of undetermined etiology involving primarily the synovial membranes and articular structures of multiple joints. The disease is often progressive and results in pain, stiffness, and swelling of joints. In late stages deformity and ankylosis develop. The diagnosis is based routinely on the persistence of arthritic symptoms over time. The application of classification systems based on qualifying symptom criteria or on decision-tree methodology also aids in establishing a diagnosis. The primary targets of inflammation are synovial membranes and articular structures. Other organs are affected as well. Inflammation, proliferation, and degeneration typify synovial membrane involvement. Joint deformities and disability result from the erosion and destruction of synovial membranes and articular surfaces. The disease course may be short and limited or progressive and severe.

Rheumatoid arthritis is usually a disease of insidious onset, although it can be abrupt. The diagnosis typically is made when several of the qualifying criteria established by the American Rheumatism Association are met. These qualifying criteria are as follows: morning stiffness lasting longer than 1 hour before improvement; arthritis involving 3 or more joints; arthritis of the hand, particularly involvement of the proximal interphalangeal (PIP) joints, metacarpophalangeal (MCP) joints, or wrist joints; bilateral involvement of joint areas (i.e., both wrists, symmetric PIP and MCP joints); positive serum rheumatoid factor (RF); rheumatoid nodules; radiographic evidence of RA.

No cure for rheumatoid arthritis is presently available. The only small molecule therapy for disease modification in rheumatoid arthritis, methotrexate, is effective in only approximately 20% of rheumatoid arthritis patients and its use is limited by toxicity issues at higher exposures. The most effective disease modifying approaches currently in use for rheumatoid arthritis rely on protein therapeutic agents that interfere with signaling by the potent proinflammatory cytokines, TNF-α (Infliximab, Adalimumab, Etanercept,) and IL-1β (Anakinra), or an anti-CD20 monoclonal antibody (Rituximab) that depletes B-cells. These biologics are expensive therapeutics, require parenteral administration, and have variable responses in patients. Furthermore, the cytokine-targeting protein therapeutics act by preventing activation of cellular receptors, which themselves activate the NF-κB signaling pathway. However, the compounds described herein can reduce or eliminate the need for administration of such expensive agents.

Inflammatory Bowel Disease (IBD) is the name of a group of disorders that cause the intestines to become inflamed (red and swollen). Inflammatory bowel disease can be painful and debilitating. It causes chronic inflammation of the digestive tract. The two most common forms of IBD are ulcerative colitis and Crohn's Disease. Both conditions inflame the lining of the digestive tract and both can cause severe bouts of watery diarrhea and abdominal pain.

Psoriasis is a common immune-mediated chronic skin disease that comes in different forms and differing levels of severity. It is a condition that is generally found on the knees, elbows, scalp, hands, feet or lower back, and generally appears as patches of raised red skin covered by a flaky white build up. It can cause intense itching and burning Atherosclerosis is the term for the process of fatty substances, cholesterol, cellular waste products, calcium and fibrin building up in the inner lining of an artery. The first symptom of a narrowing artery may be pain or cramps at times when the blood flow can't keep up with the body's demand for oxygen. For example, during exercise a person may feel chest pain because of a lack of oxygen to the heart or while walking, a person may feel leg cramps because of a lack of oxygen to the legs.

Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated.

The pharmaceutical compositions disclosed herein can have the ability to effectively treat new patient segments where proteasome inhibition and reduced toxicity is desired or warranted.

The compounds and methods described herein can be used prophylactically or therapeutically. The term "prophylactic" or "therapeutic" treatment refers to administration of a drug to a host before or after onset of a disease or condition. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom). Administering substituted quinoline compounds (including enantiomers and salts thereof) is contemplated in both a prophylactic treatment (e.g. to patients at risk for disease, such as elderly patients who, because of their advancing age, are at risk for arthritis, cancer, and the like) and therapeutic treatment (e.g. to patients with symptoms of disease or to patients diagnosed with disease).

The compounds described herein are highly active and can be administered at lower dosages with fewer and less severe side effects, adverse drug reactions, hypersensitivities, complications and toxic side effects than currently available quinoline compounds (e.g., those that non-competitively inhibit proteasomes).

An "adverse drug reaction" refers to a response to a drug that is noxious and unintended and occurs in doses for prophylaxis, diagnosis, or therapy including side effects, toxicity, hypersensitivity, drug interactions, complications, or other idiosyncrasy.

Side effects are adverse symptoms produced by a therapeutic serum level of drug. For example, the side effect can be produced by a drug's pharmacological effect on an unintended organ system.

A toxic side effect is an adverse symptom or other effect produced by an excessive or prolonged chemical exposure to a drug (e.g., digitalis toxicity, liver toxicity).

Hypersensitivities are immune-mediated adverse reactions (e.g., anaphylaxis, allergy). Drug interactions are adverse effects arising from interactions with other drugs, foods or disease states (e.g., warfarin and erythromycin, cisapride and grapefruit, loperamide and *Clostridium difficile* colitis).

Complications are diseases caused by a drug (e.g., NSAID-induced gastric ulcer, estrogen-induced thrombosis). The adverse drug reaction may be mediated by known or unknown mechanisms (e.g., Agranulocytosis associated with chloramphenicol or clozapine).

Such side effects, adverse drug reactions, hypersensitivities, complications and toxic side effects can be determined by subject observation, assays or use of animal models available in the art.

This disclosure also includes methods for modulating proteasome function to, for example, treat various diseases including multiple myeloma and mantle cell lymphoma comprising administering a therapeutically effective amount of at least one compound described herein (e.g., compounds of the formulae I-V) to a subject in need thereof. For example, the compounds and methods described herein can inhibit proteasome activity, decrease the incidence or severity of, among other conditions described herein, including cancer or inflammatory disease symptoms, decrease cancer cell growth and/or proteasome function by 5%, or 10%, or 15%, or 20%, or 25%, or 30%, or 35%, or 40%, or 45%, or 50%, or 55%, or 60%, or 65%, or %70, or 80%, or 90%, 095%, or 97%, or 99%, or any numerical percentage between 5% and 100%.

The compounds described herein can be administered composition in an amount sufficient to inhibit 20S human proteasomes (e.g., an amount sufficient to inhibit 20S human proteasomes) and/or an amount sufficient to inhibit NFκB. Such an amount can be determined or observed by in vitro or in vivo testing where proteasomal or NFκB activity is observed in the presence and absence of a compound. When the compound decreases the proteasomal or NFκB activity (relative to a control where the compound is not present with the proteasomes or the NFκB) it can be therapeutically useful. Dose response curve can be used to evaluate the concentration of compound effective for 50% inhibition of proteasomal or NFκB activity ($IC_{50}$).

For example, the chymotrypsin-like activity of proteasomes can be measured by mixing the proteasomes with a peptide linked to a label, where the label is detectable upon cleavage of the peptide.

The disclosure also relates to treatment methods that include administration of any of the compounds described herein, for example, in a composition or dosage form. As described herein the compounds are inhibitors of proteasomes. The compounds described herein are also inhibitors of the NF-κB pathway. The compounds described herein include any of the substituted quinoline compounds disclosed herein, including salt forms, enantiomers and prodrugs of such compounds. The structural modifications of the quinoline compounds described herein enhance their biological activity. Because the quinoline compounds described herein exhibit enhanced activity, only small amounts are needed and adverse drug reactions are avoided. These compounds are useful for treatment of diseases and conditions such as cancer, inflammatory diseases, inflammatory conditions, autoimmune diseases, viral infections, and others.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The terms and expressions which have been employed are used as terms of description and not of limitation, and there is no intention that in the use of such terms and expressions of excluding any equivalents of the features shown and described or portions thereof, but it is recognized that various modifications are possible within the scope of this disclosure. Thus, it should be understood that optional features, modification, and variation of the concepts herein disclosed may be resorted to by those of ordinary skill in the art, and that such modifications and variations are considered to be within the scope of this disclosure.

EXAMPLES

The present disclosure can be better understood by reference to the following examples which are offered by way of illustration. The disclosure is not limited to the examples given herein.

All manipulations of air sensitive compounds were carried out in an Mbraun drybox under a purified nitrogen atmosphere. Toluene was purified by sparging with dry nitrogen gas and water was removed by running through activated alumina systems purchased from Solv-Tex. $^{1}$H, $^{13}$C, and $^{19}$F spectra were recorded on VXR-500 spectrometers. Melting points are uncorrected and measured on a Mel-Temp II apparatus (Laboratory Devices Inc, USA) with a mercury thermometer in an open capillary tube. Ti(NMe$_2$)$_2$dpma and Ti(NMe$_2$)$_2$dpm were made following literature procedures. Ti(NMe$_2$)$_2$dpm was used for all of the quinolines synthesized, with the exceptions 31 and 32 in which Ti(NMe$_2$)$_2$dpma was used. tert-Butylisonitrile was made according to the literature procedure and purified by distillation under dry nitrogen but it may also be purchased from Sigma Aldrich. Hexanes and ethyl acetate were purchased from Mallinckrodt chemicals and used as received. Alkynes were purchased either from Sigma Aldrich or from GFC chemicals and were dried/distilled from CaO under dry nitrogen before use. Amines were purchased from Sigma Aldrich, dried over KOH and distilled under nitrogen. Palladium(II) acetate, potassium tert-butoxide and 2-(dicyclohexylphosphino)biphenyl (97%) were also purchased from Sigma Aldrich and used as received. 2-methylquinoline (1) and 3-methylquinoline (2), were purchased from TCI America. 3-phenylquinoline (3) was synthesized via literature procedure. 3-cyclohexenyl-2,5,7-trimethylquinoline (7), 2,5,7-trimethyl-3-phenylquinoline (6), 5,7-dimethyl-2,3-diphenylquinoline (12), and 2-methyl-3-phenyl-6-(N,N-dimethylamino) quinoline (34) were synthesized via a literature procedures.

Examples 1-41: Synthesis

The compounds described herein can be synthesized using titanium-catalyzed 3-component coupling reactions. The titanium chemistry effectively adds an iminyl and amine group across the triple bond of an alkyne, iminoamination, to form unsymmetrical derivatives of 1,3-diimines, as shown in Scheme I.

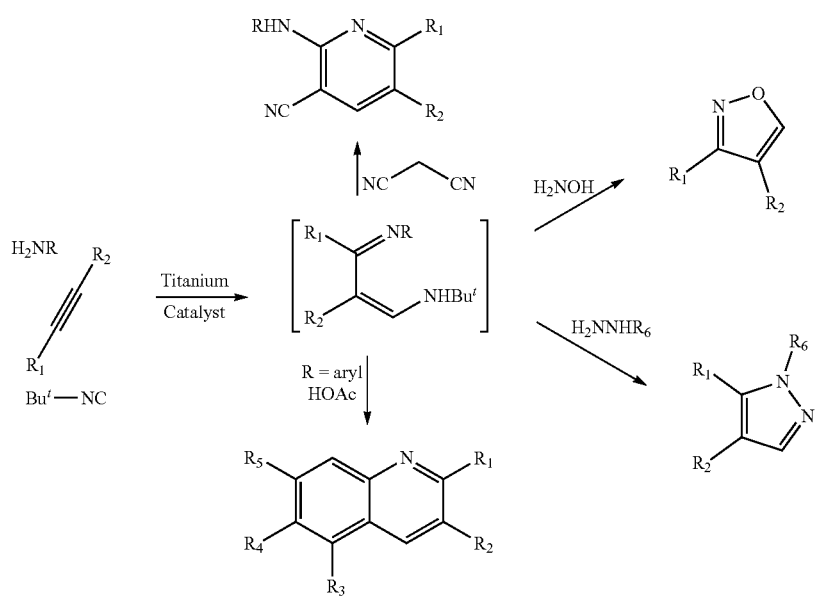

Scheme I

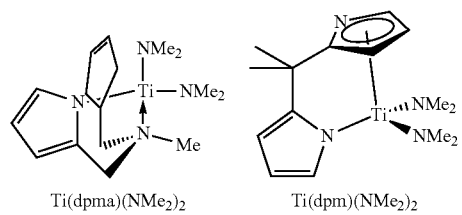

Ti(dpma)(NMe₂)₂     Ti(dpm)(NMe₂)₂

The 1,3-diimines, generated in situ, can then be applied to many different heterocyclic syntheses. The quinolines can be prepared from the 3-component coupling products using a modified Combes synthesis catalyzed by acetic acid, which rendered highly substituted frameworks in a one-pot procedure. Due to the mechanism of the formation of the imino-amination products, the quinolines are unsubstituted at the 4-position but can be substituted by a range of groups in other sites.

The two catalysts employed for the syntheses are shown at the bottom of Scheme I The ancillary ligands for titanium H₂dpma and H₂dpm (a.k.a., "protio-ligands") are both prepared in a single step from pyrrole. The catalysts can be isolated as pure compounds before use. It is possible, however, to generate the catalysts in situ from the protio-ligand and commercially available Ti(NMe₂)₄ as well.

The more reactive Ti(dpm)(NMe₂)₂ can be used for more difficult internal alkyne substrates, while milder Ti(dpma)(NMe₂)₂ can be used with sensitive terminal alkynes to avoid potential side reactions. In addition, the two catalysts can direct regioselectivity for the substrates, which broadens the structural diversity.

The compounds described herein were generally synthesized in a nitrogen filled glove box in a 10 mL pressure tube equipped with a magnetic stir bar. The titanium catalyst (0.10 mmol) is loaded into the pressure tube and dissolved in dry toluene (2 mL). The solution was loaded with the aniline derivative (1.0 mmol), alkyne derivative (1.0 mmol) and tert-butylisonitrile (1.5 mmol). The pressure tube was sealed with a Teflon screw cap, taken out of the dry box and heated at 100° C. for 24-48 h in a silicone oil bath. Volatiles were removed in vacuo, and glacial acetic acid (2 mL) was added. The mixture was then heated at 150° C. for 24 h. The pressure tube was then allowed to cool to room temperature, diluted in dichloromethane and neutralized with saturated NaHCO₃ solution. The organic layer was further extracted with additional dichloromethane, washed with brine, dried over NaSO₄, filtered and concentrated in vacuo. The crude product was dry loaded onto alumina and purification was accomplished by column chromatography on neutral alumina using hexanes/ethyl acetate (9:1, v/v) as the eluent to provide the desired quinoline.

Examples of quinolines discussed herein include those shown in Table 1.

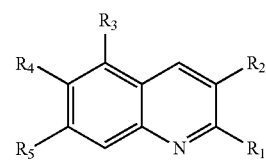

TABLE 1

| Compound | $R_1$ | $R_2$ | $R_3$ | $R_4$ | $R_5$ | $IC_{50}$ (μM) |
|---|---|---|---|---|---|---|
| 1 | $CH_3$ | H | H | H | H | >25 |
| 2 | H | $CH_3$ | H | H | H | >25 |
| 3 | H | phenyl | H | H | H | >25 |
| 4 | H | phenyl | $CH_3$ | H | $CH_3$ | 23.6 (±1.9) |
| 5 | $CH_3$ | phenyl | H | $CH_3$ | H | 19.2 (±0.3) |
| 6 | $CH_3$ | phenyl | $CH_3$ | H | $CH_3$ | 15.3 (±2.4) |
| 7 | $CH_3$ | cyclohexenyl | $CH_3$ | H | $CH_3$ | 14.4 (±0.5) |
| 8 | $CH_2CH_3$ | cyclohexenyl | $CH_3$ | H | $CH_3$ | 19.9 (±0.7) |
| 9 | H | cyclohexenyl | $CH_3$ | H | $CH_3$ | 13.8 (±1.3) |
| 10 | $CH_2CH_3$ | isopropenyl | $CH_3$ | H | $CH_3$ | >25 |
| 11 | $CH_3$ | cyclohexyl | $CH_3$ | H | $CH_3$ | 8.2 (±1.2) |
| 12 | phenyl | phenyl | $CH_3$ | H | $CH_3$ | >25 |

TABLE 1-continued

| Compound | $R_1$ | $R_2$ | $R_3$ | $R_4$ | $R_5$ | $IC_{50}$ (μM) |
|---|---|---|---|---|---|---|
| 13 | $CH_3$ | cyclohexenyl | H | H | H | >25 |
| 14 | H | cyclohexenyl | Cl | H | Cl | >25 |
| 15 | H | cyclohexenyl | Br | H | Br | >25 |
| 16 | $CH_3$ | cyclohexenyl | H | Br | H | 9.9 (±0.6) |
| 17 | $CH_3$ | cyclohexenyl | H | Cl | H | >25 |
| 18 | $CH_3$ | cyclohexenyl | H | F | H | >25 |
| 19 | $CH_3$ | cyclohexenyl | H | $CH_3$ | H | 8.5 (±0.1) |
| 20 | $CH_3$ | cyclohexenyl | H | $(CH_2)_3CH_3$ | H | 7.6 (±1.3) |
| 21 | H | cyclohexenyl | H | $N(CH_3)_2$ | H | 6.3 (±0.3) |
| 22 | $CH_3$ | cyclohexenyl | H | $N(CH_3)_2$ | H | 6.1 (±0.2) |
| 23 | $CH_2CH_3$ | cyclohexenyl | H | $N(CH_3)_2$ | H | 5.6 (±0.4) |

TABLE 1-continued

| Compound | R₁ | R₂ | R₃ | R₄ | R₅ | IC₅₀ (μM) |
|---|---|---|---|---|---|---|
| 24 | CH₃ | cyclohex-1-en-1-yl | H | morpholin-4-yl | H | 9.1 (±0.5) |
| 25 | CH₃ | cyclohex-1-en-1-yl | H | piperidin-1-yl | H | 5.4 (±0.1) |
| 26 | CH₃ | cyclohex-1-en-1-yl | H | OCH₃ | H | >25 |
| 27 | CH₃ | cyclohex-1-en-1-yl | OCH₃ | OCH₃ | OCH₃ | 15.6 (±0.7) |
| 28 | H | cyclohexyl | H | N(CH₃)₂ | H | 5.5 (±0.8) |
| 29 | CH₃ | cyclohexyl | H | N(CH₃)₂ | H | 6.7 (±0.2) |
| 30 | CH₃ | cyclohex-1-en-1-yl | H | CH(CH₃)₂ | H | 7.8 (±0.1) |
| 31 | H | C(CH₃)₃ | H | N(CH₃)₂ | H | >25 |
| 32 | (CH₂)₃CH₃ | H | H | N(CH₃)₂ | H | >25 |
| 33 | CH₂CH₃ | CH₂CH₃ | H | N(CH₃)₂ | H | 18.7 (±1.0) |
| 34 | CH₃ | phenyl | H | N(CH₃)₂ | H | 10.0 (±0.6) |
| 35 | phenyl | phenyl | H | N(CH₃)₂ | H | >25 |
| 36 | CH₃ | phenyl | H | (CH₂)₃CH₃ | H | 21.6 (±1.1) |

TABLE 1-continued

| Compound | $R_1$ | $R_2$ | $R_3$ | $R_4$ | $R_5$ | $IC_{50}$ (µM) |
|---|---|---|---|---|---|---|
| 37 | $CH_3$ | phenyl | H | $CH(CH_3)_2$ | H | >25 |
| 38 | $CH_3$ | phenyl | H | Br | H | >25 |
| 39 | $CH_3$ | cyclohexyl | H | $CH(CH_3)_2$ | H | — |
| 40 | $CH_3$ | cyclohexyl | H | $(CH_2)_3CH_3$ | H | — |
| 41 | $CH_3$ | cyclohexyl | $CH_3$ | $CH_3$ | $CH_3$ | — |

5,7-Dimethyl-3-phenylquinoline (4)

Pale yellow solid 128 mg (55%). $^1$H NMR (CDCl$_3$, 500 MHz, 20° C.): d=2.51 (3H, s, CH$_3$), 2.68 (3H, s, CH$_3$), 7.23 (1H, s, Ar—H), 7.39-7.42 (1H, m, Ar—H, 7.48-7.53 (2H, m, Ar—H), 7.68-7.70 (2H, m, Ar—H), 7.74 (1H, s, Ar—H), 8.36-8.37 (1H, d, J=2 Hz, Ar—H), 9.10 (1H, d, J=2 Hz, Ar—H). $^{13}$C NMR (CDCl$_3$, 125 MHz, 20° C.): d=18.5, 21.8, 125.3, 126.4, 127.4, 127.8, 129.1 129.6, 129.8, 132.6, 134.2, 138.4, 139.3, 147.9, 149.3. MS (EI): m/z 233 (M$^+$). Anal. Found (calcd): C, 87.42 (87.52); H, 6.52 (6.48); N, 6.06 (6.00). Mp: 76-78° C.

2,6-Dimethyl-3-phenylquinoline (5)

Pale yellow solid 158 mg (68%). $^1$H NMR (CDCl$_3$, 500 MHz, 20° C.): d=2.50 (3H, s, CH$_3$), 2.63 (3H, s, CH$_3$), 7.37-7.39 (3H, m, Ar—H), 7.40-7.43 (2H, m, Ar—H), 7.49-7.51 (2H, m, Ar—H), 7.83 (1H, s, Ar—H), 7.94-7.96 (1H, d, J=2 Hz, Ar—H). $^{13}$C NMR (CDCl$_3$, 125 MHz, 20° C.): d=21.5, 24.4, 126.2, 126.7, 127.4, 128.0, 128.3, 129.1, 131.5, 135.4, 135.6, 135.7, 140.0, 145.6, 156.2 MS (EI): m/z 233 (M$^+$). Anal. found (calcd): C, 87.62 (87.52); H, 6.42 (6.47); N, 5.96 (6.00). Mp: 80-81° C.

2-Ethyl-3-cyclohexenyl-5,7-dimethylquinoline (8)

Light yellow oil 102 mg (38%). $^1$H NMR (CDCl$_3$, 500 MHz, 20° C.): d=1.51-1.61 (7H, m) 1.99-2.03 (2H, m, CH$_2$), 2.14-2.16 (2H, m, CH$_2$), 2.21 (3H, s, CH$_3$), 2.31 (3H, s, CH$_3$), 3.04-3.09 (2H, q, J=8 Hz, CH$_2$), 5.60-5.62 (1H, m, CH), 6.86 (1H, s, Ar—H), 7.85 (1H, s, Ar—H), 8.05 (1H, s, Ar—H). $^{13}$C NMR (CDCl$_3$, 125 MHz, 20° C.): d=13.6, 18.0, 21.3, 22.0, 23.0, 25.3, 29.1, 30.8, 124.3, 126.7, 126.8, 128.4, 130.5, 133.3, 136.5, 137.9, 138.0, 148.2, 160.9. MS (EI): m/z 265 (M$^+$). HRMS, found: m/z 265.1840; calcd for C$_{19}$H$_{23}$N$^+$ 265.1830.

3-Cyclohexenyl-5,7-dimethylquinoline (9)

Pale yellow solid 99 mg (42%). $^1$H NMR (CDCl$_3$, 500 MHz, 20° C.): d=1.69-1.71 (2H, m, CH$_2$), 1.82-1.84 (2H, m, CH$_2$), 2.26-2.28 (2H, m, CH$_2$), 2.47 (3H, s, CH$_3$), 2.48-2.52 (2H, m, CH$_2$), 2.63 (3H, s, CH$_3$), 6.29-6.30 (1H, m, CH), 7.17 (1H, s, Ar—H), 7.66 (1H, s, Ar—H), 8.07-8.08 (1H, d, J=2 Hz, Ar—H), 8.94-8.95 (1H, d, J=2 Hz, Ar—H). $^{13}$C NMR (CDCl$_3$, 125 MHz, 20° C.): d=18.6, 21.7, 21.9, 22.9, 26.0, 27.3, 125.2, 126.1, 126.8, 126.9, 128.3, 129.5, 129.6, 133.9, 134.1, 134.3, 148.1. MS (EI): m/z 237 (M$^+$). Anal. found (calcd): C, 7.69 (8.07); N, 5.82 (5.90). Mp: 58-59° C.

2-Ethyl-5,7-dimethyl-3-(prop-1-en-2-yl)quinoline (10)

Pale yellow solid 158 mg (62%). $^1$H NMR (CDCl$_3$, 500 MHz, 20° C.): d=1.34-1.37 (3H, t, J=7.5 Hz, CH$_3$), 2.12 (3H, s, CH$_3$), 2.46 (3H, s, CH$_3$), 2.57 (3H, s, CH$_3$), 2.96-3.00 (2H, q, J=8 Hz, CH$_2$), 4.98-4.99 (1H, d, J=1 Hz, CH), 5.27-5.28 (1H, d, J=1 Hz, CH), 7.08 (1H, s, Ar—H), 7.67 (1H, s, Ar—H), 7.89 (1H, s, Ar—H). $^{13}$C NMR (CDCl$_3$, 125 MHz, 20° C.): d=14.1, 18.3, 21.6, 24.9, 29.1, 116.1, 123.8, 125.7, 128.4, 130.7, 133.5, 135.7, 138.4, 144.5, 147.5, 160.6. MS (EI): m/z 255 (M$^+$). Anal. found (calcd): C, 85.32 (85.2); H, 8.53 (8.50); N, 6.15 (6.22).

3-Cyclohexyl-2,5,7-trimethyl)quinoline (11)

3-Cyclohexenyl-2,5,7-trimethylquinoline (7) (60 mg, 0.024 mmol) was dissolved in 6 mL of ethanol and hydrogenated at low pressure, using a hydrogen ballon, over 10% palladium on carbon (100 mg) at room temperature (25° C.) for an hour. Purifica-tion was accomplished via filtration through neutral alumina followed by column chromatography on neutral alumina using hexanes/ethyl acetate (9:1, v/v), which afforded the desired com-pound as a pale white liquid 54 mg (90%). $^1$H NMR (CDCl$_3$, 500 MHz, 20° C.): d=1.42-1.49 (4H, m, CH$_2$), 1.79-1.82 (2H, m, CH$_2$), 1.89-1.95 (4H, m, CH$_2$), 2.46 (3H, s, CH$_3$), 2.61 (3H, s, CH$_3$), 2.73 (3H, s, CH$_3$), 2.79-2.81 (1H, m, CH), 7.10 (1H, s, Ar—H), 7.62 (1H, s, Ar—H), 7.96 (1H, s, Ar—H). $^{13}$C NMR (CDCl$_3$, 125 MHz, 20° C.): d=18.5, 22.8, 26.2, 27.1, 29.7, 33.9, 40.1, 124.7, 125.4, 128.1, 128.4, 128.5, 133.5, 138.2, 143.3, 157.3. MS (EI): m/z 253 (M$^+$). Anal. found (calcd): C, 85.29 (85.32); H, 9.23 (9.15); N. 5.48 (5.53).

3-Cyclohexenyl-2-methylquinoline (13)

Yellow liquid 60 mg (28%). $^1$H NMR (CDCl$_3$, 500 MHz, 20° C.): d=1.68-1.72 (2H, m, CH$_2$), 1.76-1.80 (2H, m, CH$_2$), 2.17-2.23 (2H, m, CH$_2$), 2.23-2.26 (2H, m, CH$_2$), 2.67 (3H, s, CH$_3$), 5.67-5.68 \(1H, m, CH), 7.40-7.43 (1H, m, Ar—H), 7.58-7.61 (1H, m, Ar—H), 7.69-7.71 (1H, d, J=9 Hz, Ar—H), 7.75 (1H, s, Ar—H), 7.96-7.98 (1H, d, J=9 Hz, Ar—H). $^{13}$C NMR (CDCl$_3$, 125 MHz, 20° C.): d=21.9, 22.9, 23.7, 25.4, 30.1, 125.6, 126.9, 127.1, 127.4, 128.2, 128.7, 134.3, 137.3, 138.1, 146.6, 157.6. MS (EI): m/z 223 (M$^+$). Anal. found (calcd): C, 86.12 (86.06); H, 7.60 (7.67); N, 6.28 (6.27).

5,7-Dichloro-3-cyclohexenyl-2-methylquinoline (14)

Brown solid 131 mg (45%). $^1$H NMR (CDCl$_3$, 500 MHz, 20° C.): d=1.70-1.73 (2H, m, CH$_2$), 1.77-1.80 (2H, m, CH$_2$), 2.18-2.23 (2H, m, CH$_2$), 2.23-2.26 (2H, m, CH$_2$), 2.65 (3H, s, CH$_3$), 5.69-5.71 (1H, m, CH), 7.46-7.47 (1H, d, J=2 Hz, Ar—H), 7.87-7.89 (1H, m, J=3 Hz, Ar—H), 8.06 (1H, s, Ar—H). $^{13}$C NMR (CDCl$_3$, 125 MHz, 20° C.): d=21.9, 22.8, 23.6, 25.4, 29.9, 123.6, 126.4, 126.7, 128.3, 130.9, 131.6, 133.6, 136.7, 139.3, 147.2, 159.9. MS (EI): m/z 292 (M+). Anal. found (calcd): C, 65.81 (65.77); H, 5.20 (5.17); N, 4.72 (4.79). Mp: 56-58° C.

5,7-Dibromo-3-cyclohexenyl-2-methylquinoline (15)

Yellow solid 122 mg (32%). $^1$H NMR (CDCl$_3$, 500 MHz, 20° C.): d=1.71-1.73 (2H, m, CH$_2$), 1.78-1.80 (2H, m, CH$_2$), 2.20-2.23 (2H, m, CH$_2$), 2.24-2.26 (2H, m, CH$_2$), 2.66 (3H, s, CH$_3$), 5.71-5.72 (1H, m, CH), 7.80-7.81 (1H, d, J=2 Hz, Ar—H), 8.01 (1H, s, Ar—H), 8.11-8.12 (1H, d, J=2 Hz, Ar—H). $^{13}$C NMR (CDCl$_3$, 125 MHz, 20° C.): d=21.9, 22.8, 23.5, 25.4, 29.9, 121.8, 121.9, 125.2, 128.4, 130.7, 132.1, 133.5, 136.7, 139.8, 147.4, 159.9. MS (EI): m/z 381 (M$^+$). Anal. found (calcd): C, 50.51 (50.43); H, 3.93 (3.97); N, 3.64 (3.68). Mp: 89-90° C.

6-Bromo-3-cyclohexenyl-2-methylquinoline (16)

Light brown oil 103 mg (34%)$^1$H NMR (C$_6$D$_6$, 500 MHz, 20° C.): d=1.45-1.54 (4H, m, CH$_2$), 1.93-1.96 (4H, m, CH$_2$), 2.60 (3H, s, CH$_3$), 5.41-5.42 (1H, m, CH), 7.13 (1H, s, Ar—H), 7.38-7.40 (1H, dd, J=2 Hz, 9 Hz, Ar—H), 7.58-7.59 (1H, d, J=2 Hz, Ar—H), 7.88-7.90 (1H, d, J=9 Hz, Ar—H). $^{13}$C NMR (C$_6$D$_6$, 125 MHz, 20° C.): d=21.9, 22.8, 23.6, 25.3, 29.7, 119.2, 127.2, 128.2, 129.2, 130.7, 131.8, 132.7, 137.1, 138.6, 145.7, 157.8. MS (EI): m/z 301 (M$^+$). HRMS, found: m/z 301.0480; calcd for C$_{16}$H$_{16}$BrN$^+$ 301.0466.

6-Chloro-2-methyl-3-cyclohexenylquinoline (17)

Light yellow oil 54 mg (21%). $^1$H NMR (CDCl$_3$, 500 MHz, 20° C.): d=1.72-1.75 (2H, quin, J=11 Hz, CH$_2$), 1.79-1.82 (2H, quin, J=12 Hz, CH$_2$), 2.21 (2H, m, CH$_2$), 2.25 (2H, m, CH$_2$), 2.67 (3H, s, CH$_3$), 6.32 (1H, m CH), 7.54-7.57 (1H, dd, J=2 Hz, 9 Hz, Ar—H), 7.69 (1H, s, Ar—H), 7.70-7.71 (1H, d, J=3 Hz, Ar—H), 7.91-7.93 (1H, d, J=9 Hz, Ar—H). $^{13}$C NMR (CDCl$_3$, 125 MHz, 20° C.): d=21.9, 22.9, 23.7, 25.4, 30.0, 125.8, 127.6, 127.9, 129.6, 129.8, 131.2, 133.5, 136.9, 139.1, 144.9, 158.2. MS (EI): m/z 257 (M$^+$). HRMS, found: m/z 257.0963; calcd for C$_{16}$H$_{16}$ClN$^+$ 257.0971.

3-Cyclohexenyl-6-fluoro-2-methylquinoline (18)

Brown oil 38 mg (15%). $^1$H NMR (CDCl$_3$, 500 MHz, 20° C.): d=1.69-1.71 (2H, m, CH$_2$), 1.72-1.78 (2H, m, CH$_2$), 2.17-2.19 (2H, m, CH$_2$), 2.20-2.25 (2H, m, CH$_2$), 2.65 (3H, s, CH$_3$), 5.67-5.68 (1H, m, CH), 7.29-7.31 (1H, dd, J=3 Hz, 9 Hz, Ar—H), 7.34-7.38 (1H, ddd, J=3 Hz, 9 Hz, 9 Hz, Ar—H), 7.70 (1H, s, Ar—H), 7.94-7.97 (1H, dd, J=6 Hz, 10 Hz, Ar—H). $^{13}$C NMR (CDCl$_3$, 125 MHz, 20° C.): d=21.9, 22.9, 23.5, 25.4, 30.0, 110.0-110.1 (d, J$_{CF}$=21 Hz), 118.6-118.8 (d, J$_{CF}$=26 Hz), 127.4-127.5 (d, J$_{CF}$=10 Hz), 127.7, 130.5-130.6 (d, J$_{CF}$=9 Hz), 133.7-133.8 (d, J$_{CF}$=5 Hz), 137.0, 138.9, 143.7, 157.0-157.1 (d d, J$_{CF}$=3 Hz), 159.1. $^{19}$F NMR (CDCl$_3$, 470 MHz, 20° C.): d=115.0 (m). MS (EI): m/z 241 (M$^+$). Anal. found (calcd): C, 79.59 (79.64); H, 6.65 (6.68); N, 5.75 (5.80).

3-Cyclohexenyl-2,6-dimethylquinoline (19)

Brown oil 123 mg (52%). $^1$H NMR (CDCl$_3$, 500 MHz, 20° C.): d=1.68-1.72 (2H, m, CH$_2$), 1.75-1.78 (2H, m, CH$_2$), 2.17-2.20 (2H, m, CH$_2$), 2.22-2.24 (2H, m, CH$_2$), 2.46 (3H, s, CH$_3$), 2.64 (3H, s, CH$_3$), 5.65-5.67 (1H, m, CH), 7.42-7.45 (2H, m, Ar—H), 7.66 (1H, s, Ar—H), 7.85-7.86 (1H, d, J=9 Hz, Ar—H). $^{13}$C NMR (CDCl$_3$, 125 MHz, 20° C.): d=21.4, 22.0, 22.9, 23.6, 25.4, 30.1, 126.0, 126.9, 127.3, 127.9, 130.9, 133.7, 135.3, 137.4, 138.1, 145.3, 156.6. MS (EI): m/z 237 (M$^+$). Anal. found (calcd): C, 86.04 (86.03); H, 8.09 (8.07); N, 5.87 (5.90).

4.1.14. 6-Butyl-3-cyclohexenyl-2-methylquinoline (20)

Viscous yellow oil 87 mg (32%). $^1$H NMR (CDCl$_3$, 500 MHz, 20° C.): d=0.94-0.96 (3H, t, J=7 Hz, CH$_3$), 1.35-1.43 (2H, sext, J=15 Hz, CH$_2$), 1.65-1.71 (2H, quin, J=15 Hz, CH$_2$), 1.71-1.76 (2H, quin, J=11 Hz, CH$_2$), 1.79-1.84 (2H, quin, J=10 Hz, CH$_2$), 2.22 (2H, m, CH$_2$), 2.27 (2H, m, CH$_2$), 2.68 (3H, s, CH$_3$), 2.76-2.79 (2H, t, J=8 Hz, CH$_2$), 5.70 (1H, s, CH), 7.48-7.50 (2H, m, Ar—H), 7.73 (1H, s, Ar—H) 7.91-7.93 (1H, d, J=9 Hz, Ar—H). $^{13}$C NMR (CDCl$_3$, 125 MHz, 20° C.): d=14.0, 22.1, 22.3, 23.0, 23.6, 25.5, 30.2, 33.5, 35.6, 125.5, 126.9, 127.3, 127.9, 130.4, 134.0, 137.4, 138.1, 140.3, 145.4, 156.7. MS (EI): m/z 279 (M$^+$). HRMS, found: m/z 280.2062; calcd for C$_{20}$H$_{26}$N$^+$ 280.2065.

3-Cyclohexenyl-6-(N,N-dimethylamino)quinoline (21)

Viscous yellow oil 97 mg (38%). $^1$H NMR (CDCl$_3$, 500 MHz, 20° C.): d=1.41-1.46 (2H, m, CH$_2$), 1.52-1.57 (2H, m, CH$_2$), 1.95-1.97 (2H, m, CH$_2$), 2.23-2.4 (2H, m, CH$_2$), 2.51 (6H, s, N(CH$_3$)$_2$), 6.08-6.1 (1H, m, CH), 6.64-6.65 (1H, d, J=3 Hz, Ar—H), 6.95-6.97 (1H, dd, J=3 Hz, 9 Hz, Ar—H), 7.67-7.69 (1H, d, J=2 Hz, Ar—H), 8.26-8.28 (1H, d, J=9 Hz, Ar—H), 9.03-9.04 (1H, d, J=2 Hz, Ar—H). $^{13}$C NMR (CDCl$_3$, 125 MHz, 20° C.): d=22.0, 22.8, 25.8, 26.9, 39.9, 105.3, 118.5, 125.9, 128.2, 129.6, 130.1, 134.3, 135.0, 142.1, 144.9, 148.6. MS (EI): m/z 252 (M$^+$). HRMS, found: m/z 252.1634; calcd for C$_{17}$H$_{20}$N$^+$ 252.1626.

3-Cyclohexenyl-2-methyl-6-(N,N-di methylamino) quinoline (22)

Brown solid 117 mg (44%). $^1$H NMR (CDCl$_3$, 500 MHz, 20° C.): d=1.72-1.74 (2H, m, CH$_2$), 1.75-1.78 (2H, m, CH$_2$), 2.22-2.24 (2H, m, CH$_2$), 2.25-2.29 (2H, m, CH$_2$), 2.64 (3H, s, CH$_3$), 3.04 (6H, s, N(CH$_3$)$_2$), 5.68-5.70 (1H, m, CH), 6.78-6.79 (1H, d, J=3 Hz, Ar—H), 7.29-7.32 (1H, dd, J=3 Hz, 9 Hz, Ar—H), 7.63 (1H, s, Ar—H), 7.86-7.88 (1H, d, J=9 Hz, Ar—H). $^{13}$C NMR (CDCl$_3$, 125 MHz, 20° C.): d=22.1, 23.0, 23.2, 25.4, 30.1, 40.8, 105.2, 118.8, 126.8, 128.2, 128.8, 132.7, 137.7, 138.3, 140.8, 148.2, 153.1. MS (EI): m/z 266 (M$^+$). Anal. found (calcd): C, 81.14 (81.16); H, 8.40 (8.32); N, 10.46 (10.52). Mp: 81-83° C.

3-Cyclohexenyl-2-ethyl-6(N,N-dimethylamino)quinoline (23)

Viscous light yellow oil 109 mg (39%). $^1$H NMR (CDCl$_3$, 500 MHz, 20° C.): d=1.52-1.60 (7H, m), 1.98-2.01 (2H, m, CH$_2$), 2.12-2.17 (2H, m, CH$_2$), 2.52 (6H, s, N(CH$_3$)$_2$), 3.03-3.07 (2H, quart, J=7 Hz, CH$_2$), 5.59 (1H, m), 6.65 (1H, d, J=3 Hz, Ar—H), 6.98-7.00 (1H, dd, J=3 Hz, 9 Hz, Ar—H), 7.50 (1H, s, Ar—H), 8.20-8.22 (1H, d, J=9 Hz, Ar—H). $^{13}$C NMR (CDCl$_3$, 125 MHz, 20° C.): d=13.7, 22.1, 23.1, 25.4, 28.9, 30.7, 40.1, 105.1, 118.7, 126.3, 128.2, 128.4, 129.7, 132.7, 138.0, 141.9, 148.0, 157.2. MS (EI): m/z 280 (M$^+$). HRMS, found: m/z 280.1928; calcd for C$_{19}$H$_{24}$N$^+$ 280.1939.

3-Cyclohexenyl-2-methyl-6-morpholinylquinoline (24)

A pressure tube was loaded with Pd(OAc)$_2$ (0.4 mg, 2 nmol), 2-(dicyclohexylphosphino)biphenyl (1.4 mg, 4 nmol), and KO$^t$Bu (53 mg, 48 mmol) under nitrogen atmosphere. Anhydrous toluene was added followed by 6-bromo-3-cyclohexenyl-2-methylquino-line (120 mg, 40 mmol) and morpholine (41 µL, 48 mmol). The tube was sealed, and then the mixture was stirred for 18 h at 110° C. After cooling, the mixture was diluted with dichloro-methane (20 mL) and washed with water (20 mL), and then brine (20 mL). The organic phase was dried over MgSO$_4$, and then the solvent was removed in vacuo. Purification was accomplished by column chromatography on neutral alumina. The eluent was hexanes/ethyl acetate (19:1, v/v), which afforded the desired com-pound as a viscous brown oil 63 mg (51%). $^1$H NMR (CDCl$_3$, 500 MHz, 20° C.): d=1.68-1.78 (4H, m, CH$_2$), 2.18-2.22 (4H, m, CH$_2$), 2.62 (3H, s, CH$_3$), 3.21-3.23 (4H, m, NCH$_2$), 3.85-3.89 (4H, m, OCH$_2$), 5.63-5.67 (1H, m, CH), 6.94-6.95 (1H, d, J=3 Hz, Ar—H), 7.63 (1H, s, Ar—H), 7.88-7.90 (2H, d, J=5 Hz, Ar—H), 8.00-8.02 (2H, d, J=5 Hz, Ar—H). $^{13}$C NMR (CDCl$_3$, 125 MHz, 20° C.): d=22.0, 0.6, 66.8, 121.5, 127.2, 127.8, 128.2, 128.8, 129.6, 132.9, 133.5, 138.5, 148.8, 154.7. MS (EI): m/z 308 (M$^+$). Anal. found (calcd): C, 77.81 (77.89); H, 7.80 (7.84); N, 9.01 (9.08).

3-Cyclohexenyl-2-methyl-6-piperidinylquinoline (25)

A pressure tube was loaded with Pd(OAc)$_2$ (0.3 mg, 1.6 nmol), 2-(dicyclohexylphosphino)biphenyl (1.1 mg, 3.3 nmol), and KOtBu (44 mg, 39 mmol) under nitrogen atmosphere. Anhydrous toluene was added followed by 6-bromo-3-cyclohexenyl-2-methylquinoline (100 mg, 33 mmol) and piperidine (40 µL, 40 mmol). The tube was sealed, and then the mixture was stirred for 18 h at 110° C. After cooling, the mixture was diluted with dichloromethane (20 mL) and washed with water (20 mL), and then brine (20 mL). The organic phase was dried over MgSO$_4$, and then the solvent was removed in vacuo. Purification was accomplished by column chromatography on neutral alumina. The eluent was hexane/ethyl acetate (19:1, v/v), which afforded the desired compound as a vis-cous brown oil 42 mg (42%). $^1$H NMR (CDCl$_3$, 500 MHz, 20° C.): d=1.56-1.60 (2H, m, CH$_2$), 1.61-1.78 (8H, m, CH$_2$), 2.17-2.23 (4H, m, CH$_2$), 2.61 (3H, s, CH$_3$), 3.21-3.23 (4H, m, NCH$_2$), 5.64-5.65 (1H, m, CH), 6.94-6.95 (1H, d, J=3 Hz, Ar—H), 7.51-7.54 (1H, m, Ar—H), 7.60 (1H, s, Ar—H), 7.82-7.84 (2H, d, J=10 Hz, Ar—H). $^{13}$C NMR (CDCl$_3$, 125 MHz, 20° C.): d=22.0, 23.0, 23.2, 24.3, 25.4, 25.7, 30.1, 50.8, 128.3, 128.6, 129.6, 130.0, 132.9, 133.3, 137.6, 138.2, 149.7, 154.2, 166.5. MS (EI): m/z 306 (M$^+$). Anal. Found (calcd): C, 82.36 (82.31); H, 8.49 (8.55); N, 9.15 (9.14).

3-Cyclohexenyl-6-methoxy-2-methylquinoline (26)

Brown solid 108 mg (43%). $^1$H NMR (CDCl$_3$, 500 MHz, 20° C.): d=1.72-1.75 (2H, m, CH$_2$), 1.80-1.82 (2H, m, CH$_2$), 2.22-2.23 (2H, m, CH$_2$), 2.25-2.28 (2H, m, CH$_2$), 2.66 (3H, s, CH$_3$), 3.89 (3H, s, OCH$_3$), 5.69-5.70 (1H, m, CH), 7.00-7.01 (1H, d, J=3 Hz, Ar—H), 7.27-7.30 (1H, dd, J=3 Hz, 9 Hz, Ar—H), 7.69 (1H, s, Ar—H), 7.89-7.91 (1H, d, J=9 Hz, Ar—H). $^{13}$C NMR (CDCl$_3$, 125 MHz, 20° C.): d=22.0, 22.9, 23.3, 25.4, 30.1, 55.4, 104.8, 121.1, 127.2, 127.7, 129.7, 133.4, 137.4, 138.4, 142.7, 154.9, 157.1. MS (EI): m/z 253 (M$^+$). Anal. found (calcd): C, 80.49 (80.60); H, 7.60 (7.56); N, 5.57 (5.53). Mp: 50-52° C.

3-Cyclohexenyl-5,6,7-trimethoxy-2-methylquinoline (27)

Viscous light yellow oil 131 mg (42%). $^1$H NMR (CDCl$_3$, 500 MHz, 20° C.): d=1.71-1.76 (2H, m, CH$_2$), 1.79-1.84 (2H, m, CH$_2$), 2.23 (2H, m, CH$_2$), 2.27 (2H, m, CH$_2$), 2.65 (3H, s, CH$_3$), 3.97 (3H, s, OCH$_3$), 3.99 (3H, s, OCH$_3$), 4.06 (3H, s, OCH$_3$), 5.69 (1H, s, Ar—H), 7.20 (1H, s, Ar—H), 7.98 (1H, s, Ar—H). $^{13}$C NMR (CDCl$_3$, 125 MHz, 20° C.): d=22.0, 23.0, 23.4, 25.5, 30.3, 56.1, 61.2, 61.6, 103.2, 117.8, 127.4, 129.0, 136.0, 137.5, 140.3, 144.3, 146.8, 155.4, 156.8. MS (EI): m/z 313 (M$^+$). HRMS, found: m/z 314.1763; calcd for C$_{19}$H$_{24}$NO$^+$ 314.1756. Mp: 93-95° C.

3-Cyclohexyl-6-(N,N-dimethylamino)quinoline (28)

3-cyclohexenyl-6-(N,N-dimethylamino)quinoline (21) (80 mg, 0.32 mmol) was dissolved in 6 mL of ethanol and hydrogenated at low pressure, using a hydrogen ballon, over 10% palladium on car-bon (120 mg) at room temperature (25° C.) overnight. Purification was accomplished via filtration through neutral alumina followed by column chromatography on neutral alumina using hexanes/ethyl acetate (9:1, v/v), which afforded the desired compound as a viscous light yellow oil 75 mg (93%). $^1$H NMR (CDCl$_3$, 500 MHz, 20° C.): d=1.07-1.11 (1H, m, CH$_2$), 1.18-1.22 (2H, m, CH$_2$), 1.27-1.33 (2H, m, CH$_2$), 1.58-1.60 (1H, m, CH$_2$), 1.64-1.68 (2H, m, CH$_2$), 1.74-1.77 (2H, m, CH$_2$), 2.33-2.38 (1H, m, CH), 2.52 (6H, s, N (CH$_3$)$_2$), 6.65-6.66 (1H, d, J=3 Hz, Ar—H), 6.97-6.99 (1H, dd, J=3 Hz, 9 Hz, Ar—H), 7.52 (1H, d, J=2 Hz, Ar—H), 8.26-8.28 (1H, d, J=9 Hz, Ar—H), 8.71-8.72 (1H, d, J=2 Hz, Ar—H). $^{13}$C NMR (CDCl$_3$, 125 MHz, 20° C.): d=26.0, 26.7, 34.0, 40.0, 42.0, 105.1, 118.4, 129.8, 128.9, 130.2, 140.2, 142.1, 147.4, 148.4. MS (EI): m/z 254 (M+). HRMS, found: m/z 254.1774; calcd for C$_{17}$H$_{22}$N$_2$+254.1783.

3-Cyclohexyl-2-methyl-6-(N,N-dimethylamino)quinoline (29)

2-Methyl-3-cyclohexenyl-6-(N,N-dimethylamino)quinoline (22) (100 mg, 0.38 mmol) was dissolved in 6 mL of ethanol and hydrogenated at low pressure, using a hydrogen ballon, over 10% palladium on carbon (150 mg) at room temperature (25° C.) over-night. Purification was accomplished via filtration through neutral alumina followed by column chromatography on neutral alumina using hexanes/ethyl acetate (9:1, v/v), which afforded the desired compound as a viscous yellow oil 98 mg (97%). $^1$H NMR (CDCl$_3$, 500 MHz, 20° C.): d=1.16-1.33 (4H, m, CH$_2$), 1.63-1.79 (4H, m, CH$_2$), 2.55 (6H, s, CH$_3$), 2.71 (3H, s, CH$_3$), 6.72-6.73 (1H, d, J=3 Hz, Ar—H), 6.99-7.01 (1H, dd, J=3 Hz, 9 Hz, Ar—H), 7.63 (1H, s, Ar—H), 8.20-8.22 (1H, d, J=9 Hz, Ar—H). $^{13}$C NMR (CDCl$_3$, 125 MHz, 20° C.): d=25.6, 26.3, 27.0, 33.7, 39.9, 40.2, 105.3, 118.4, 129.0, 129.5, 129.6, 139.2, 141.3, 148.0, 153.4. MS (EI): m/z 268 (M$^+$). HRMS, found: m/z 268.1934; calcd for C$_{18}$H$_{24}$N$^+$ 268.1939.

3-Cyclohexenyl-6-isopropyl-2-methylquinoline (30)

Viscous yellow oil 112 mg (43%). $^1$H NMR (CDCl$_3$, 500 MHz, 20° C.): d=1.32-1.34 (6H, d, J=7 Hz, CH$_3$), 1.71-1.75 (2H, quin, J=11 Hz, CH$_2$), 1.78-1.83 (2H, quin, J=12 Hz, CH$_2$), 2.21 (2H, m, CH$_2$), 2.26 (2H, m, CH$_2$), 2.68 (3H, s, CH$_3$), 3.02-3.11 (1H, sept, J=7 Hz, CH), 5.69 (1H, s, CH), 7.53 (1H, s, Ar—H), 7.53-7.55 (1H, app d, J=9 Hz, Ar—H), 7.75 (1H, s, Ar—H), 7.94-7.96 (1H, d, J=9 Hz, Ar—H). $^{13}$C NMR (C$_6$D$_6$, 125 MHz, 20° C.): d=22.0, 23.0, 23.5, 23.7, 25.3, 30.0, 34.0, 123.3, 126.8, 127.1, 128.3, 129.0, 133.6, 137.7, 137.8, 145.7, 146.5, 156.3. MS (EI): m/z 265 (M$^+$). HRMS, found: m/z 266.1907; calcd for C$_{15}$H$_{20}$N$^+$ 266.1909.

3-tert-Butyl-6-(N,N-dimethylamino)quinoline (31)

Viscous light brown oil 55 mg (24%). $^1$H NMR (CDCl$_3$, 500 MHz, 20° C.): d=1.20 (9H, s, C(CH$_3$)$_3$), 2.53 (6H, s, N(CH$_3$)$_2$), 6.67-6.68 (1H, d, J=3 Hz, Ar—H), 6.98-7.01 (1H, dd, J=3 Hz, 9 Hz, Ar—H), 7.72-7.73 (1H, d, J=3 Hz, Ar—H), 8.26-8.27 (1H, d, J=9 Hz, Ar—H), 8.96-8.98 (1H, d, J=2 Hz, Ar—H). $^{13}$C NMR (CDCl$_3$, 125 MHz, 20° C.): d=30.6, 33.3, 40.0, 105.3, 118.4, 128.4, 129.5, 130.0, 141.5, 143.0, 146.0, 148.5. MS (EI): m/z 228 (M$^+$). HRMS, found: m/z 228.1617; calcd for C$_{15}$H$_{20}$N$^+$ 228.1626.

2-Butyl-6-(N,N-dimethylamino)quinoline (32)

Viscous brown oil 69 mg (30%). $^1$H NMR (CDCl$_3$, 500 MHz, 20° C.): d=0.86-0.89 (3H, t, J=7 Hz, CH$_3$), 1.32-1.39 (2H, sext, J=7 Hz, CH$_2$), 1.82-1.88 (2H, quin, J=7 Hz, CH$_2$), 2.50 (6H, s, N (CH$_3$)$_2$), 2.92-2.95 (2H, t, J=7 Hz, CH$_2$), 6.64-6.65 (1H, d, J=3 Hz, Ar—H), 6.92-6.93 (1H, d, J=8 Hz, Ar—H), 6.98-7.01 (1H, dd, J=3 Hz, 9 Hz, Ar—H), 7.61-7.63 (1H, d, J=8 Hz, Ar—H), 8.19-8.21 (1H, d, J=9 Hz, Ar—H). $^{13}$C NMR (CDCl$_3$, 125 MHz, 20° C.): d=13.9, 22.6, 31.9, 39.5, 40.0, 105.4, 119.1, 121.4, 128.1, 130.1, 133.8, 142.9, 148.0, 158.4. MS (EI): m/z 228 (M$^+$). HRMS, found: m/z 228.1616; calcd for C$_{15}$H$_{20}$N$^+$ 228.1626.

2,3-Diethyl-N,N-dimethylquinoline (33)

Light brown solid 74 mg (33%). $^1$H NMR (CDCl$_3$, 500 MHz, 20° C.): d=1.32-1.35 (3H, t, J=7 Hz, CH$_3$), 1.35-1.38 (3H, t, J=7 Hz, CH$_3$), 2.78-2.83 (2H, q, J=7 Hz, CH$_2$), 2.95-2.99 (2H, q, J=7 Hz, CH$_2$), 3.06 (6H, s, N(CH$_3$)$_2$), 6.79 (1H, d, J=2.8 Hz, Ar—H), 7.29-7.31 (1H, dd, J=3 Hz, 9 Hz, Ar—H), 7.71 (1H, s, Ar—H), 7.89-7.91 (1H, d, J=9 Hz, Ar—H). $^{13}$C NMR (CDCl$_3$, 125 MHz, 20° C.): d=13.9, 14.5, 25.1, 28.5, 41.9, 105.0, 118.6, 128.7, 128.9, 132.5, 135.2, 148.2, 158.8. MS (EI): m/z 228 (M$^+$). HRMS, found: m/z 229.1712; calcd for C$_{15}$H$_{20}$N$^+$ 229.1705. Mp: 64-66° C.

2,3-Diphenyl-6-(N,N-dimethylamino)quinoline (35)

Dark yellow solid 90 mg (28%). $^1$H NMR (CDCl$_3$, 500 MHz, 20° C.): d=2.52 (1H, s, N(CH$_3$)$_2$), 6.63-6.64 (1H, d, J=3 Hz, Ar—H), 7.01-7.06 (5H, m, Ar—H), 7.07-7.10 (2H, m, Ar—H), 7.19-7.21 (2H, m, Ar—H), 7.72-7.74 (3H, m, Ar—H), 8.30-8.32 (1H, d, J=9 Hz, Ar—H). $^{13}$C NMR (CDCl$_3$, 125 MHz, 20° C.): d=39.9, 104.6, 119.4, 126.7, 127.2, 127.53, 128.0, 128.9, 129.8, 130.4, 130.5, 134.7, 135.6, 141.2, 141.4, 142.3, 148.5, 153.9. MS (EI): m/z 324 (M$^+$). HRMS, found: m/z 324.1642; calcd for C$_{23}$H$_{20}$N$^+$ 324.1626. Mp: 159-161° C.

6-Butyl-2-methyl-3-phenylquinoline (36)

Viscous yellow oil 101 mg (37%). $^1$H NMR (CDCl$_3$, 500 MHz, 20° C.): d=0.95-0.98 (3H, t, J=7 Hz, CH$_3$), 1.37-1.45 (2H, sext, J=10 Hz, CH$_2$), 1.68-1.74 (2 J, quin, J=10 Hz, CH$_2$), 2.67 (3H, s, CH$_3$), 2.79-2.82 (2H, t, J=5 Hz, CH$_2$), 7.41-7.44 (3H, m, Ar—H), 7.47-7.50 (2H, m, Ar—H), 7.56-7.57 (2H, m, Ar—H), 7.91 (1H, s, Ar—H), 7.99-8.01 (1H, d, J=9 Hz, Ar—H). $^{13}$C NMR (CDCl$_3$, 125 MHz, 20° C.): d=14.0, 22.4, 24.4, 33.5, 35.6, 125.7, 126.8, 127.5, 128.1, 128.4, 129.2, 131.0, 135.6, 135.7, 140.1, 140.8, 145.8, 156.3. MS (EI): m/z 275 (M$^+$). HRMS, found: m/z 276.1750; calcd for C$_{20}$H$_{22}$N$^+$ 276.1752.

6-Isopropyl-2-methyl-3-phenylquinoline (37)

Viscous yellow oil 143 mg (55%). $^1$H NMR (CDCl$_3$, 500 MHz, 20° C.): d=1.35-1.37 (2H, d, J=7 Hz, CH$_3$), 2.67 (3H, s, CH$_3$), 3.06-3.15 (1H, sept, J=8 Hz, CH), 7.40-7.44 (3H, m, Ar—H), 7.47-7.50 (2H, m, Ar—H), 7.60 (1H, s, Ar—H), 7.61-7.64 (1H, dd, J=9 Hz, Ar—H), 7.93 (1H, s, Ar—H), 8.01-8.03 (1H, d, J=9 Hz, Ar—H). $^{13}$C NMR (CDCl$_3$, 125 MHz, 20° C.): d=23.9, 24.5, 29.7, 34.1, 123.5, 126.8, 127.5, 128.2, 128.4, 129.2, 129.3, 135.6, 135.9, 140.1, 145.9, 146.7, 156.4. MS (EI): m/z 261 (M$^+$). HRMS, found: m/z 262.1596; calcd for C$_{19}$H$_{20}$N$^+$ 262.1593.

6-Bromo-2-methyl-3-phenylquinoline (38)

Light tan solid 337 mg (26%, on 5 mmol scale). $^1$H NMR (CDCl$_3$, 500 MHz, 20° C.): d=2.66 (3H, s, CH$_3$), 7.39-7.41 (2H, m, Ar—H), 7.43-7.46 (1H, m, Ar—H), 7.48-7.52 (2H, m, Ar—H), 7.76-7.78 (1H, dd, J=2 Hz, 9 Hz, Ar—H), 7.87 (1H, s, Ar—H), 7.93-7.95 (1H, d, J=9 Hz, Ar—H), 7.95-7.96

(1H, d, J=2 Hz, Ar—H). $^{13}$C NMR (CDCl$_3$, 125 MHz, 20° C.): d=24.7, 119.7, 127.8, 128.0, 128.5, 129.1, 129.4, 130.2, 132.7, 134.9, 136.6, 139.4, 145.6, 158.0. MS (EI): m/z 297 (M$^+$). HRMS, found: m/z 298.0230; calcd for C$_{16}$H$_{13}$BrN$^+$. Mp: 88-90° C.

Example 41: Biological Evaluation

Proteasomal activity measurement: The fluorogenic substrates Suc-LLVY-AMC, Z-ARR-AMC, and Z-LLE-AMC were used to measure CT-L, T-L and casp-L proteasome activities, respectively. Assays were carried out in black, clear bottom 96 well plates in a 200 μL reaction volume containing 1 nM of purified human 20S proteasome in 50 mM Tris-HCL pH 7.5 and 0.03% SDS containing 50 IM fluorogenic substrate at 37° C. The rate of cleavage of fluorogenic peptide substrates was determined by monitoring the fluorescence of released aminomethylcoumarin using a SpectraMax M5e multiwall plate reader at an excitation wavelength of 380 nm and emission wavelength of 460 nm. Fluo-rescence was measured every minute over a period of 30 minutes and the maximum increase in fluorescence per minute was used to calculate specific activities of each sample.

NF-κB-luc reporter assay: HeLa NF-κB-luc cells (5.0× 10$^5$ cells/mL) were seeded into a 96-well white opaque plate using DMEM medium supplemented with 5% fetal bovine serum, 500 U/mL penicillin, 100 μg/mL streptomycin, 1 mM sodium pyruvate, 0.2 mM L-glutamine, and 100 Ig/mL hygromycin B. After 24 h the cell culture medium was replaced with DMEM medium supplemented with 100 U/mL penicillin and 100 Ig/mL streptomycin. Cell cultures were pretreated with vehicle (1% DMSO), 50 IMpeptide aldehyde MG-132 (positive control) or quinoline (final concentrations were 50, 25, 12.5, 6.25, 3.13 and 1.56 IM) for 30 min at 37° C. in 5% CO$_2$. TNF-α was added to a final concentration of 25 ng/mL and the samples were further incubated for 8 h at 37° C. in 5% CO$_2$. Cells were assayed for firefly luciferase production using the Steady-Glo luciferase reporter assay (Promega, Madison, WI) according to manufacturer's protocol. The luminescence of each well was measured using a Veritas microplate luminometer. All reported data are the average of two independent experiments unless otherwise indicated. The data was analyzed using GraphPad Prism 4.0. The data was normalized to TNF-α activation and the EC50 values were calculated using the equation for the sigmodial curve for variable slope.

Compounds were screened in vitro using purified human 20S proteasome and the fluorogenic peptide substrate, Suc-LLVY-AMC, as the substrate for CT-L activity as described herein. The rates of hydrolysis were monitored by fluorescence increase at 37° C. over 30 min, and the linear portion of the curves were used to calculate the IC$_{50}$ values. Of the compounds tested, some of the quinolines exhibited low micromolar efficacies for 20S proteasome inhibition.

Of the quinolines tested, quinoline 7 exhibited modest inhibition of the 20S chymotryptic activity with an IC$_{50}$ of 14.4 μM. Compounds 7 was therefore selected for further evaluation and optimization. It appeared that substitutions in the R$_1$, R$_2$, R$_3$. and R$_5$ positions were important to see inhibition of proteasome activity. See Table 1.

Quinoline 7 was subsequently evaluated for its inhibition of the proteasome's tryptic (b2)-like and caspase (b1)-like activity in vitro using purified human 20S proteasome and the following fluorogenic peptide as substrates: Boc-LRR-AMC (substrate for T-L activity) and Z-LLE-AMC (substrate for casp-L activity). The data shows that the quinoline 7 inhibits the casp-L at a similar IC$_{50}$ (IC$_{50}$ 17.7 μM) as the chymotryptic activity, but not the tryp-tic-L activities of the 20S catalytic core (IC$_{50}$>25 μM).

The mechanism by which quinoline 7 inhibits the proteasome was investigated using Michaelis-Menton analysis to determine of K$_M$ and V$_{max}$ and then further illustrated using a Lineweaver-Burk double reciprocal plot of the kinetic data. Kinetic analysis of CT-L activity of purified 20S particles indicate that when the substrate (Suc-LLVY-AMC) concentration was increased incrementally and measurements were taken at five different concentrations of compound 7 or vehicle, the V$_{max}$ of the CT-L activity decreases and the K$_M$ increases, with the increasing concentration of substrate. While not wishing to be bound by any specific theory, this is a pattern that is consistent with mixed-type inhibition, and is consistent with an allosteric-type modulation of proteasome activity, where binding of the quinoline 7 occurs at a site different from the active site, resulting in inhibition of enzyme activity.

In order to evaluate whether the inhibition of proteasome activity translated in cell culture, we evaluated compound 7 for inhibition of NE-KB regulation. Inhibition of the proteasome affects multiple critical signaling pathways and the anti-cancer activity of proteasome inhibitors has been linked, in part, to their ability to inhibit the pro-inflammatory, anti-apoptotic NE-KB signaling pathway. The nuclear transcription factor, NF-κB is sequestered in the cytoplasm by the inhibitory protein κB, termed IκB. Activation of the NE-KB pathway by cytokines, such as TNF-α, results in the rapid ubiquitinylation and proteasomal degradation of IκB, which releases NF-κB for nuclear translocation and gene transcription. Proteasome inhibitors prevent IκB from proteolytic degrading and result in an accumulation of cytosolic ubiquitinylated IκB following TNF-α activation. In order to determine if quinoline 7 affects NE-KB mediated gene transcription, we evaluated quinoline 7 in HeLa NE-KB-luc cells.

Cell cultures were pretreated with vehicle (1% DMSO), the proteasome inhibitor MG-132 (positive control) or compound 7 (final concentrations were 50, 25, 12.5, 6.25, 3.13, 1.56 μM) 30 min at 37° C. in 5% CO$_2$. TNF-α was added to a final concentration of 25 ng/mL, and the samples were further incubated for 8 h at 37° C. in 5% CO$_2$ and subsequently assayed for firefly luciferase production using the Steady-Glo luciferase reporter assay. The in vitro inhibition of the proteasome by quinoline 7 translated well in cell culture and prevented NE-KB mediated gene transcription with an IC$_{50}$ value of 12.1 μM in a dose-response manner.

Example 42: Kinetic Solubility Assay

Seven three-fold dilutions from 300 μM were prepared in phosphate buffered saline (ph=7.4) and 1% DMSO. Each concentration for each compound was tested three times (n=3). The compounds were incubated for 2 hours at 37° C. and the absorbance at 620 nm was evaluated for each dilution. Mebendazole was used as a control. The estimated kinetic solubility for compounds to is shown in Table 2.

TABLE 2

| Compound | Solubility (μM) |
|---|---|
| 7 | 38.1 |
| 11 | 128.8 |
| 34 | 121.4 |
| 20 | 14.5 |

TABLE 2-continued

| Compound | Solubility (μM) |
|---|---|
| 23 | 27.4 |
| 29 | 138.4 |
| 30 | 11.7 |
| Mebendazole (control) | 32.3 |

Example 43: Microsome (S9 Fraction) Stability Assay

The assay set up is summarized in Table 3.

TABLE 3

| | |
|---|---|
| Final test compound concentration | 3 μM |
| Number of Replicates | n = 4 |
| Microsome species | S9 fraction (mouse) |
| Microsome concentration | 0.25 mg/mL |
| Buffer | 100 mM phosphate buffer (pH 7.4), 3 mM MgCl$_2$ |
| Cofactor | NADPH |
| Final DMSO concentration | 1% |
| Time point(s) | 30 minutes |
| Test compound requirements | 300 μL of a 30 mM DMSO solution |
| Analysis method | LC-MS/MS |
| Data | Percent microsome remaining |

The assay results are shown in Table 4.

TABLE 4

| Compound | Mouse microsomes remaining (% remaining at 30 minutes) |
|---|---|
| 7 | 18 |
| 11 | 100 |
| 34 | >100 |
| 20 | 12 |
| 23 | 5 |
| 29 | 4 |
| 30 | 6 |
| Imipramine (control) | 25 |

What is claimed:

1. A compound of the formula III:

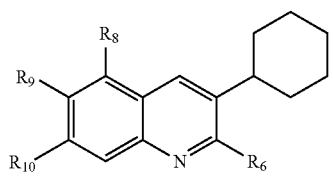

wherein:
$R_6$ is alkyl;
$R_8$ is alkyl;
$R_9$ is hydrogen, halogen, hydroxy, alkyl, alkoxy, aminoalkyl or heterocyclyl; and
$R_{10}$ is alkyl.

2. The compound of claim 1, wherein $R_6$, $R_8$ or $R_{10}$ is lower alkyl.

3. The compound of claim 1, wherein $R_6$, $R_8$ or $R_{10}$ is methyl.

4. The compound of claim 1, wherein $R_9$ is hydrogen, lower alkyl, lower alkoxy, N,N-dimethylamino or a heterocyclyl group optionally containing one additional heteroatom.

5. The compound of claim 1, wherein $R_9$ is methyl, isopropyl butyl or methoxy.

6. The compound of claim 1, wherein $R_9$ is piperidinyl or a morpholinyl group.

7. A compound of the formula IV:

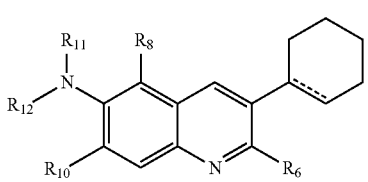

wherein:
the dashed line represents a single or a double bond;
$R_6$ is hydrogen, alkyl or aryl;
$R_8$ is hydrogen, halogen, or alkyl;
$R_{10}$ is hydrogen, halogen, alkyl, or alkoxy; and
$R_{11}$ is H and $R_{12}$ is alkyl or, $R_{11}$ and $R_{12}$, together with the nitrogen atom to which they are attached, form a heterocyclyl group optionally containing one additional heteroatom.

8. The compound of claim 7, wherein $R_6$, $R_8$ or $R_{10}$ is lower alkyl.

9. The compound of claim 7, wherein $R_6$, $R_8$ or $R_{10}$ is methyl.

10. A compound of the formula:

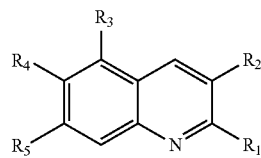

wherein:

| $R_1$ | $R_2$ | $R_3$ | $R_4$ | $R_5$ |
|---|---|---|---|---|
| CH$_3$ | | CH$_3$ | H | CH$_3$ |

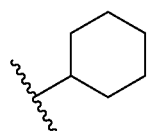 [SMILES: *C1CCCCC1]

-continued

| R₁ | R₂ | R₃ | R₄ | R₅ |
|---|---|---|---|---|
| H | cyclohexenyl | H | N(CH₃)₂ | H |
| CH₃ | cyclohexenyl | H | N(CH₃)₂ | H |
| CH₂CH₃ | cyclohexenyl | H | N(CH₃)₂ | H |
| CH₃ | cyclohexenyl | H | morpholinyl (N-linked) | H |
| CH₃ | cyclohexenyl | H | piperidinyl (N-linked) | H |
| H | cyclohexyl | H | N(CH₃)₂ | H |
| CH₃ | cyclohexyl | H | N(CH₃)₂ | H |
| H | C(CH₃)₃ | H | N(CH₃)₂ | H |
| (CH₂)₃CH₃ | H | H | N(CH₃)₂ | H |
| CH₂CH₃ | CH₂CH₃ | H | N(CH₃)₂ | H |
| phenyl | phenyl | H | N(CH₃)₂ | H |
| CH₃ | cyclohexyl | CH₃ | CH₃ | CH₃. |

11. A pharmaceutical composition comprising one or more compounds of claim 1 and one or more pharmaceutically acceptable excipients.

12. A pharmaceutical composition comprising one or more compounds of claim 7 and one or more pharmaceutically acceptable excipients.

13. A pharmaceutical composition comprising one or more compounds of claim 10 and one or more pharmaceutically acceptable excipients.

14. A method for treating multiple myeloma and/or mantle cell lymphoma, the comprising administering a therapeutically effective amount of at least one compound of claim 1 to a subject in need thereof.

15. A method for treating multiple myeloma and/or mantle cell lymphoma, the comprising administering a therapeutically effective amount of at least one compound of claim 7 to a subject in need thereof.

16. A method for treating multiple myeloma and/or mantle cell lymphoma, the comprising administering a therapeutically effective amount of at least one compound of claim 10 to a subject in need thereof.

17. A method for inhibiting proteasome function comprising administering a therapeutically effective amount of at least one compound of claim 1 to a subject in need thereof.

18. A method for inhibiting proteasome function comprising administering a therapeutically effective amount of at least one compound of claim 7 to a subject in need thereof.

19. A method for inhibiting proteasome function comprising administering a therapeutically effective amount of at least one compound of claim 10 to a subject in need thereof.

* * * * *